(12) United States Patent
Nahata et al.

(10) Patent No.: US 9,446,261 B2
(45) Date of Patent: Sep. 20, 2016

(54) BILLING SYSTEM FOR VIDEO PROVISIONING SYSTEM

(75) Inventors: Hans Raj Nahata, New Providence, NJ (US); Sanjay Mishra, North Potomac, MD (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 818 days.

(21) Appl. No.: 13/196,650

(22) Filed: Aug. 2, 2011

(65) Prior Publication Data

US 2012/0079513 A1 Mar. 29, 2012

Related U.S. Application Data

(60) Provisional application No. 61/387,939, filed on Sep. 29, 2010.

(51) Int. Cl.
| | |
|---|---|
| *H04N 7/16* | (2011.01) |
| *A61N 5/06* | (2006.01) |
| *H04N 21/2225* | (2011.01) |
| *H04N 21/258* | (2011.01) |
| *H04N 21/2668* | (2011.01) |
| *H04N 21/431* | (2011.01) |
| *H04N 21/472* | (2011.01) |
| *H04N 21/475* | (2011.01) |
| *H04N 21/84* | (2011.01) |
| *H04N 21/8549* | (2011.01) |

(52) U.S. Cl.
CPC ........ *A61N 5/0618* (2013.01); *H04N 21/2225* (2013.01); *H04N 21/25891* (2013.01); *H04N 21/2668* (2013.01); *H04N 21/4316* (2013.01); *H04N 21/4755* (2013.01); *H04N 21/47202* (2013.01); *H04N 21/84* (2013.01); *H04N 21/8549* (2013.01)

(58) Field of Classification Search
CPC ..................... H04N 21/225; H04N 21/25891; H04N 21/2668; H04N 21/4316; H04N 21/47202; H04N 21/4755
USPC ....................................................... 725/1, 5
See application file for complete search history.

(56) References Cited

U.S. PATENT DOCUMENTS

| | | | |
|---|---|---|---|
| 2008/0235104 A1* | 9/2008 | Chow et al. ..................... 705/26 |
| 2010/0107201 A1* | 4/2010 | Hannum et al. ................. 725/99 |
| 2011/0214149 A1* | 9/2011 | Schlacht ......................... 725/58 |

* cited by examiner

*Primary Examiner* — Farzana Hossain

(57) ABSTRACT

A method, performed by a video provisioning system, may include receiving a request to purchase a video asset from a user device. The method may further include determining an account type associated with the user device; billing the purchase to a bundled services account, where the bundled services account is associated with one or more of a television service, a data connection service, or a telephone service delivered over a same connection, when the account type corresponds to the bundled services account; billing the purchase to a voice services account, where the voice services account corresponds to a telephone service, when the account type corresponds to the voice services account; and processing a payment for the purchase via an online payment service, when the user device is not associated with a bundles services account or a voice services account.

10 Claims, 18 Drawing Sheets

| USER DEVICE 642 | CONTENT 644 | TRANSACTION 646 | CONTENT MARKER 648 | CATALOG 650 | PARENTAL CONTROLS 652 | GLOBAL PARENTAL CONTROLS 654 |
|---|---|---|---|---|---|---|
| CD | ASSET 1 | PURCHASE | | 235-1 | PC1 | PC4 |
| WHD | ASSET 2 | RENTAL | MARKER 2 | 235-2 | PC2 | PC4 |
| STB | ASSET 3 | SUBSCRIPTION | | 220 | PC3 | PC4 |
| ⋮ | | | ⋮ | | ⋮ | |

640 →

660 — (row 1)
662 — (row 2)
664 — (row 3)

BILLING SYSTEM FOR VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND INFORMATION

Video content may be available from many sources and may be delivered to users through a variety of methods. For example, video content may be available from commercial broadcasting television networks (e.g., ABC, CBS, NBC, FOX, etc.) via free broadcast; from a cable television service (e.g., CNN, TNT, TBS, etc.) for a periodic subscription fee; from a satellite television service (e.g. DirectTV, Dish Network, etc.) for a periodic subscription fee; from a pay-per-view service; from an on-demand video service; from a over-the-top (OTT) content providers on the Internet (e.g., Hulu, Veoh, Jaman, YouTube, etc.); and/or from any other commercial supplier (e.g., iTunes, Netflix, Blockbuster, etc.). Video content may be delivered to users, for example, via a set top box, a computer device, a wireless mobile device. Managing billing of video content purchases, associated with various sources and/or delivery methods, may be challenging.

BRIEF DESCRIPTION OF THE DRAWINGS

FIGS. 6B and 6C are diagrams of example fields that may be stored in the profile memory of FIG. 6A;

DETAILED DESCRIPTION OF PREFERRED EMBODIMENTS

Figure 1:
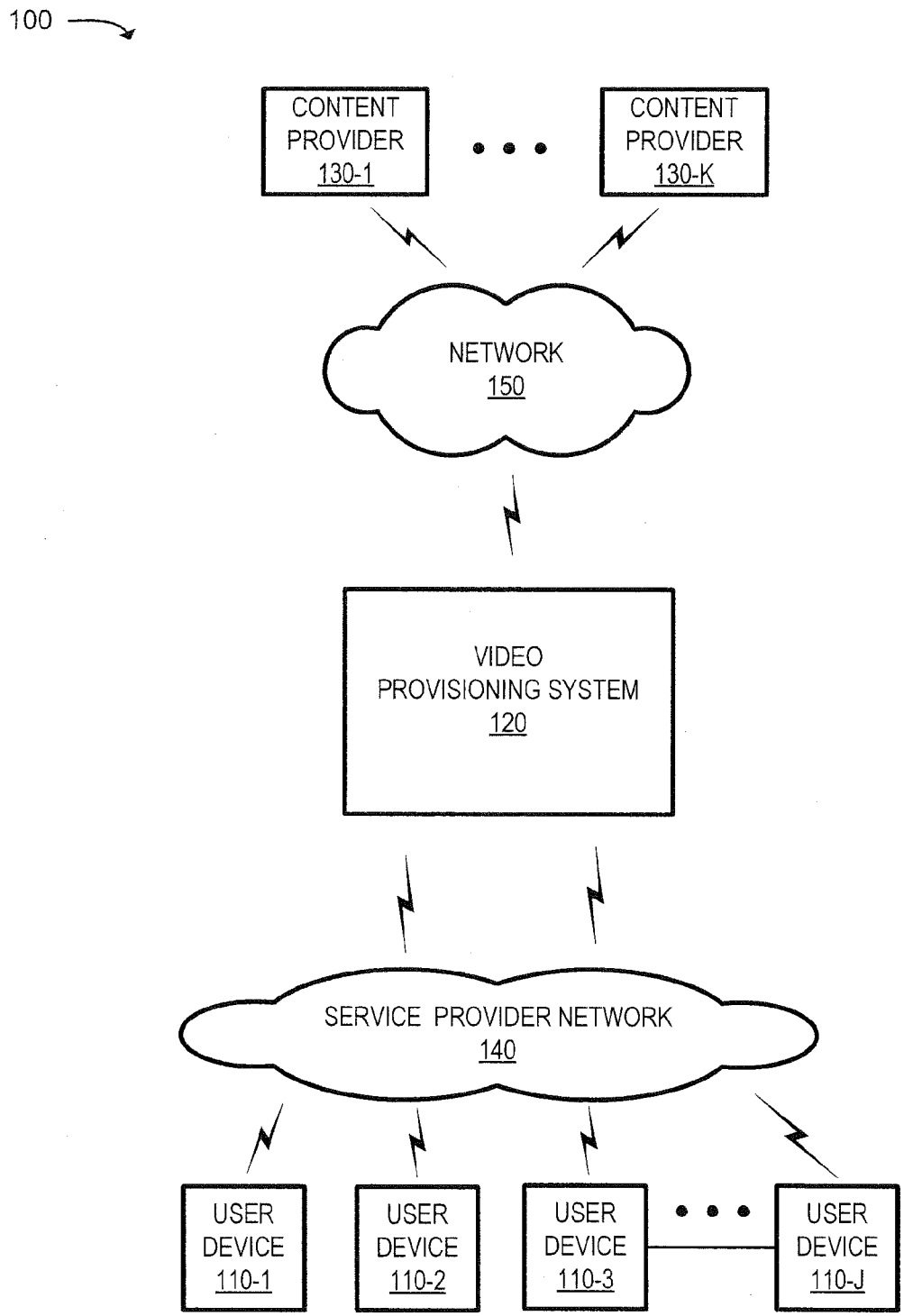
FIG. 1 is a diagram illustrating an example environment according to an implementation described herein.

The following detailed description refers to the accompanying drawings. The same reference numbers in different drawings identify the same or similar elements.

An implementation described herein may relate to billing a customer for a purchase of a video asset made via a video provisioning system (VPS). The VPS may enable a customer to purchase and consume video content using different types of user devices, including a set top box, a computer device, and/or a wireless mobile device. Customers associated with different types of accounts may be able to purchase a video asset using the VPS and bill the purchase to an associated account. Furthermore, the VPS may enable the customer to consume (e.g., view) the purchased video asset using any number of different devices registered with the VPS.

An implementation described herein may relate to determining an account type associated with a user device. A customer may have a bundled services account. A bundled services account may be associated with one or more of a television service, a telephone service, and/or a data (e.g., Internet connection) service delivered over a same connection (e.g., a fiberoptic connection, a coaxial connection, a wireless connection, etc.). For example, a customer may have a fiberoptic connection to a service provider and the service provider may provide a television service, a telephone service, and an Internet connection over the fiberoptic connection. In another example, the customer may have a fixed wireless connection to a service provider and the service provider may provide a television service, a telephone service, and an Internet connection over the fixed wireless connection.

The customer need not subscribe to all available services over the connection in order to have a bundled services account. For example, a customer may subscribe only to a television service delivered over the connection, in which case the customer may be provided with a set top box and have a bundles services account. In another example, the customer may subscribe only to a telephone service over the connection or only to a data (e.g., Internet) connection over the connection, in which case the customer may not be provided with a set top box and still have a bundles services account. In yet other examples, a customer may subscribe to both a television service and a data connection service; to a television service and a telephone service; to a data connection service and telephone service; or to television, telephone, and data connection service. Regardless of how many of the available services the customer subscribes to over a particular connection, the customer may have a bundled services account, since the bundled services account may be associated with the particular connection.

An implementation described herein may enable a customer with a bundled services account to purchase a video asset through the VPS using any device capable of communicating with the VPS. The VPS may determine that the customer has a bundled services account, without requiring the customer to provide information about the bundled services account, and may bill the purchase to the customer's bundled services account. Thus, the purchase of the video asset may appear on the customer's next bill for the bundled services. Furthermore, the VPS may enable the customer to consume (e.g., view) the purchased video asset using any number of different devices registered with the VPS.

A customer may have a voice services account. The voice services account may provide the customer with telephone services. In one example, the voice services account may be associated with a wireless connection (e.g., a mobile telephone service). In another example, the voice services account may be associated with a wired (e.g., a landline) connection. In one example, the wired connection may be associated with a legacy telephone service.

An implementation described herein may enable a customer with a voice services account to purchase a video asset through the VPS using any device capable of communicating with the VPS. The VPS may determine that the customer has a voice services account, without requiring the customer to provide information about the voice services account, and may bill the purchase to the customer's voice services account. Thus, the purchase of the video asset may appear on the customer's next bill for the voice services.

A customer may not have a pre-existing account associated with the VPS. An implementation described herein may enable a customer to create an online account that may enable the customer to purchase a video asset using the online account and pay for the purchase using an online payment method, such as a credit card. Thus, the VPS may automatically determine an account type for the customer, if the customer is accessing the VPS using any number of different devices registered with the VPS, and may add the purchase to an appropriate bill for the customer.

Furthermore, if a customer with an existing bundled services account or a voice services account purchases a video asset through the VPS and later cancels the bundled services account or the voice services account, a profile associated with the customer may be converted to an online account, enabling the customer to continue to be able to access and consume any video assets purchased through the VPS.

FIG. 1 is a diagram of an example environment in which the systems and/or methods, described herein, may be implemented. As shown in FIG. 1, environment 100 may include a group of user devices 110-1, . . . , 110-J (where J≥1) (referred to herein collectively as "user devices 110" and individually as "user device 110"), a video provisioning system (VPS) 120, a group of content providers 130-1, . . . , 130-K (where K≥1) (referred to herein collectively as "content providers 130" and individually as "content provider 130"), a service provider network 140, and a network 150. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, and/or another type of computation or communication device.

User device 110 may communicate with VPS 120 and/or perform certain operations to obtain a video asset from VPS 120. For example, user device 110 may access a portal (e.g., a website, a user interface, an interactive program guide (IPG), an interactive media guide (IMG), etc.) associated with VPS 120, to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Although FIG. 1 shows example components of environment 100, in other implementations, environment 100 may include fewer components, different components, differently arranged components, or additional components than depicted in FIG. 1. Additionally or alternatively, one or more components of environment 100 may perform functions described as being performed by one or more other components of environment 100.

Figure 2:
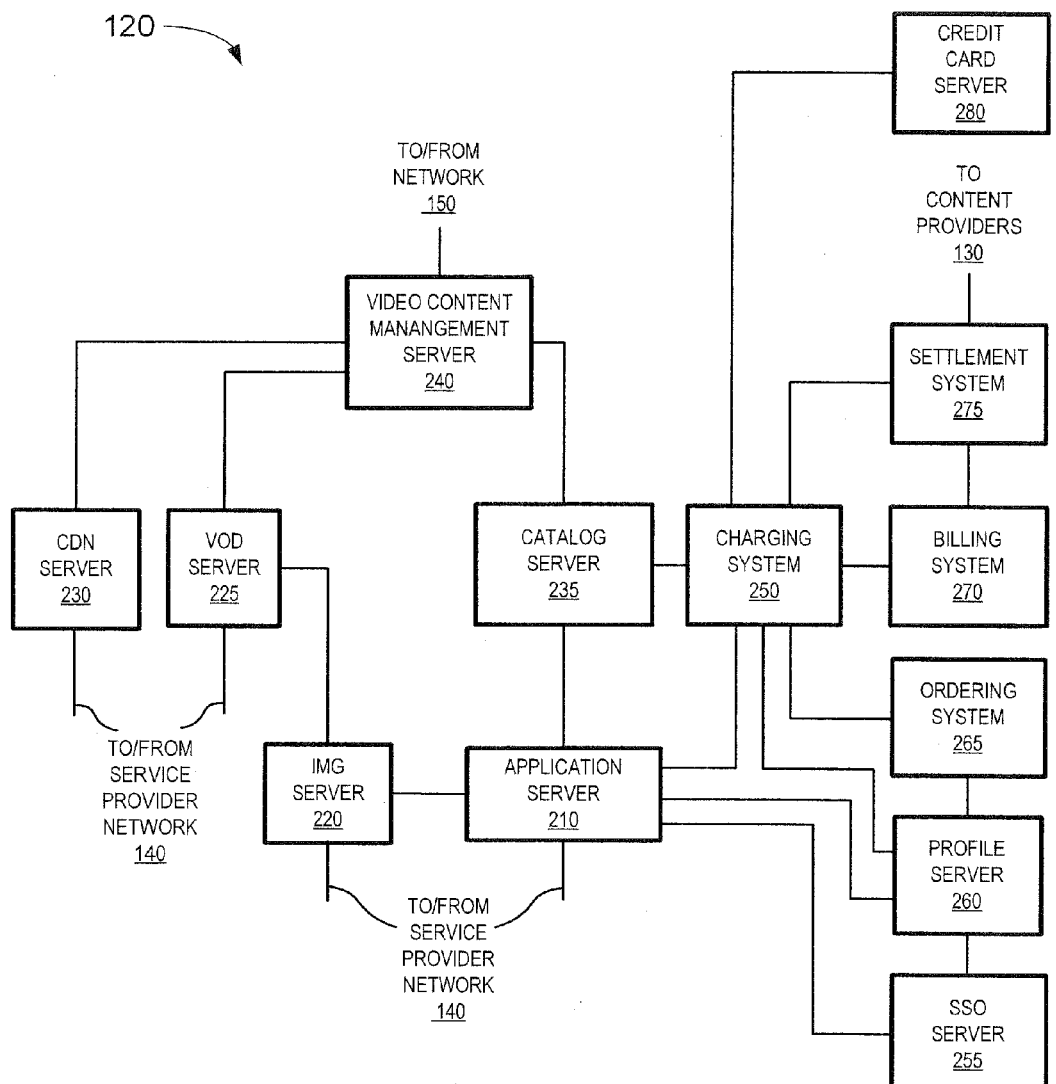
FIG. 2 is a diagram illustrating example components associated with the video provisioning system of FIG. 1.

FIG. 2 is a diagram of example devices associated with VPS 120. As shown in FIG. 2, VPS 120 may include an application server 210, an interactive media guide (IMG) server 220, a video on-demand (VOD) server 225, a content delivery network (CDN) server 230, a catalog server 235, a video content management (VCM) server 240, a charging system 250, a single sign-on (SSO) server 255, a profile server 260, an ordering system 265, a billing system 270, a settlement system 275, and a credit card server 280.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing an a store front portal (i.e., via an IMG), that can be accessed by the set top box, and application server 210 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 210 may be combined into a single device that provisions the store front portal for each type of user device 110. In another example, the store front portal may be provisioned, for each type of user device 110, by another device and/or network instead of, or in combination with, IMG server 220 and/or application server 210. Thus, the examples below are provided for explanatory purposes only.

Application server 210 may include one or more server devices, or other types of computation or communication devices, that gather, process, search, store, and/or provide information in a manner similar to that described herein. Application server 210 may receive metadata that has been published by catalog server 235.

Metadata may enable the video assets to be identified, managed, offered, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, an on-line asset, etc.); a text description, a key word index, and/or summary of the video asset; an image (e.g., cover art) associated with the video asset, and/or information associated with artists associated with the video asset (e.g., names of actors, directors, producers, etc.). The metadata may also, or alternatively, include information associated with a type of video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

The metadata may be associated with video assets that are to be made available and/or offered (e.g., for sale, rent, subscription, etc.) to user devices 110. Application server 210 may host a portal (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The portal may enable SSO portal access, to a user of one or more user devices 110, based on the same login credentials (e.g., username, password, personal identification number (PIN), etc.). Application server 210 may publish all or a portion of the metadata to the portal that permits any of user devices 110 to browse, perform searches, process payment, etc. for video assets based on the metadata that is published to the portal.

Application server 210 may store information associated with a transaction history that corresponds to a type of user device 110 (e.g., a computer user device 110, a wireless handheld user device 110, a gaming user device 110, etc.) that is different than a set top box user device 110. The transaction history may include information regarding prior transactions (e.g., purchases, rentals, subscriptions, etc.), associated with one or more video assets, by user device 110. The transaction history may also identify a period of time during which a rental period or subscription period, for a video asset, is valid. Application server 210 may, in another example, transmit information, associated with the transaction history, to profile server 260, to be stored in a user profile associated with a user of user device 110.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 210). The metadata may be associated with video content that may be obtained by a particular type of user device 110, such as a set top box user device 110.

IMG server 220 may publish all or a portion of the metadata to an IMG UI that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 210, which may permit the set top box user device 110 to access the metadata associated video assets that are stored in CDN server 230.

IMG server 220 may store information associated with a transaction history that corresponds to a set top box user device 110. The transaction history may include information regarding prior transactions (e.g., purchases, rentals, subscriptions, etc.), associated with one or more video assets, by set top box user device 110. The transaction history may also identify a period of time during which a rental period or subscription period, for a video asset, is valid. Application server 210 may, in another example, transmit information, associated with the transaction history, to profile server 260, to be stored in a user profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may publish a portion of the metadata, associated with video assets (e.g., that are available for release and/or not subject to a blackout, etc.), to IMG server 220. In another example implementation, VOD server 225 may communicate with content provider 130 to receive video content directly from content provider 130 (e.g., not via VCM server 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata, associated with the video assets, may include identifiers (e.g., video asset numbers, titles, etc.), prices (e.g., sale prices, rental prices, subscription prices, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front portal associated with VPS application server 210. Catalog server 235 may not publish metadata associated with video assets that are identified as not yet being available.

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 210. VCM server 240 may publish the one or more formats, associated with the processed video assets, to VOD server 225 and/or CDN server 230.

VCM server 240 may also ingest, process, and/or publish metadata associated with the video assets. VCM server 240 may process the metadata to ensure that the metadata is supported by the different types of user devices 210. VCM server 240 may publish the processed metadata to catalog server 235.

Charging system 250 may include one or more server devices, or other types of computation or communication devices, that gather, process, search, store, and/or provide information in a manner similar to that described herein. Charging system 250 may, for example, receive a request for a purchase from application server 210. The request may include information identifying a video asset that a customer has requested to purchase, a type of requested purchase (e.g., buy, rent, subscription, etc.), and/or information identifying either the customer or the user device that the customer has used to submit the request. Charging system 250 may compute charges associated with the purchase. Charging system 250 may access catalog server 235 to obtain information about charges associated with the video asset based on, for example, the type of purchase.

Charging system 250 may request profile information from ordering system 265. For example, if a customer, that has requested a purchase, does not have an existing VPS profile, charging system 250 may request information about a bundled services profile or about a voice services profile associated with the customer. Charging system 250 may receive information about the bundles services profile or the voice services profile from ordering system 265 and may provide the information to profile server 260, along with a request to generate a VPS profile for the customer based on the information.

Charging system 250 may determine an account type associated with the customer. If the customer has an existing VPS profile, an account type may be stored in the VPS profile and may be provided to charging system 250 by application server 210 in connection with the purchase request. If the customer does not have an existing VPS profile, charging system 250 may determine the account type based on information received from ordering system 265. If ordering system 265 does not include information about any accounts associated with the customer, charging system 250 may determine that the customer does not have a pre-existing account and may designate the account type as an "online only" account. An "online only" account may indicate that the purchase may not be billed to a bill associated with another account of the customer and may indicate that the customer needs to pay for the purchase at the time of the purchase using an online payment system, such as a credit card.

Charging system 250 may instruct billing system 270 to include the computed charges for the purchase of the video asset on a next bill associated with the determined account type for the customer. For example, if the account type corresponds to a bundled services account, charging system 250 may instruct billing system 270 to include the charges on a next bundled services bill (e.g., television, Internet, and/or telephone bill) for the customer. As another example, if the account type corresponds to a voice services account, charging system 250 may instruct billing system 270 to include the charges on a next voice services (e.g., mobile telephone bill) for the customer. Charging system 250 may perform a credit check with billing system 270 to make sure the customer has enough credit associated with the determined account to add the purchase to the bill associated with the account. If billing system 270 responds to charging system 250 with an indication that the customer does not have enough credit, charging system 250 may not add the purchase to the bill associated with the determined account. Instead, charging system 250 may request that the customer pay for the purchase using an online payment method.

If charging system 250 determines that the determined account type corresponds to an "online only" account, charging system 250 may request that the customer pay for the purchase using an online payment system. For example, charging system 250 may request credit card information from the customer and may submit the purchase to credit card server 280.

Charging system 250 may determine a settlement payment for the purchase based on an agreement with content provider 130 associated with the purchased video asset. Charging system 250 may inform settlement system 275 about the purchase and may instruct settlement system 275 to settle with content provider 130.

SSO server 255 may include one or more server devices, or other types of computation or communication devices, that gather, process, search, store, and/or provide information in a manner similar to that described herein. SSO server 255 may, for example, perform SSO authentication for a customer. For example, a customer may access application server 210 by entering a username and password via a login page associated with a web page portal provided by application server 210. As another example, the customer may access application server 210 using a media manager application and the media manager application may submit the username and password to application server 210 on behalf of the customer. Application server 210 may submit the username and password to SSO server 255 and SSO server 255 may authentication the customer if the username and password correspond to a username and password stored at SSO server 255.

Profile server 260 may include one or more server devices, or other types of computation or communication devices, that gather, process, search, store, and/or provide information in a manner similar to that described herein. Profile server 245 may, for example, store information associated with a profile that includes information regarding the user and/or each user device 110 that the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a compression/decompression (CODEC) identifier, etc.), and/or information associated with a type of user device 110, such as a computer device (e.g., a lap top computer, a tablet computer, etc.), a wireless mobile device (e.g., a Droid®, a Blackberry®, an iPhone®, etc.), a set top box, a gaming device, etc.

The information associated with the profile may also include a respective transaction history (e.g., prior purchases, prior URLs accessed, prior downloads, etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc. Profile server 245 may communicate with application server 210 to obtain a first transaction history, associated with user device 110, that are different types of user devices 110 than a set top box user device 110, such as a computer user device 110, a wireless handheld user device 110, a gaming user device 110, etc. Profile server 245 may communicate with IMG server 220 to obtain a second transaction history, associated with a set top box user device 110. Profile server 245 may store information obtained from the first transaction history and/or the second transaction history in a user profile associated with a user of the set top box user device 110 and/or user device 110.

Ordering system 265 may include one or more server devices, or other types of computation or communication devices, that gather, process, search, store, and/or provide information in a manner similar to that described herein. Ordering system 265 may maintain information associated with a bundled services profile and/or a voice services profile associated with a customer. For example, when a customer places an order for bundled services, ordering system 265 may generate a bundled services profile for the customer. The bundled services profile may include information identifying one or more user devices associated with the customer (e.g., a set top box device), may include a username and password associated with the customer, and/or may include billing information associated with the bundled services account. The billing information may be used by billing system 270 to generate a bill for the bundled services at particular intervals (e.g., a monthly bill). As another example, when a customer places an order for voice services, ordering system 265 may generate a voice services profile for the customer. The bundled services profile may include information identifying one or more user devices associated with the customer (e.g., a mobile communication device), may include a username and password associated with the customer, and/or may include billing information associated with the voice services account. The billing information may be used by billing system 270 to generate a bill for the voice services at particular intervals (e.g., a monthly telephone bill).

Billing system 270 may include one or more server devices, or other types of computation or communication devices, that gather, process, search, store, and/or provide information in a manner similar to that described herein. Billing server 270 may, for example, generate a bill at particular intervals for a bundled services account and/or a voice services account associated with the customer. Billing system 270 may receive information about charges to be included in the bill from charging system 250. Charging system 250 may determine charges that are to be included in each bill from ordering system 265. Furthermore, billing server 250 may receive a request from charging server 250 to add charges for a purchase of a video asset to a bill associated with the customer's bundled services account or associated with the customer's voice services account.

Settlement system 275 include one or more server devices, or other types of computation or communication devices, that gather, process, search, store, and/or provide information in a manner similar to that described herein. Settlement system 275 may process settlements with content providers 130 for purchases of video assets made via VPS 120. For example, settlement system 275 may receive information about a purchase of a video asset from charging system 250 and may receive a request from charging system 250 to settle with content provider 130 associated with the purchased video asset. In one example, a settlement amount for a purchase of a video asset may be determined by charging system 250 based on an agreement made with content provider 130 associated with the purchased video asset. The information about the agreement may be stored, for example, in catalog server 235. In another example, the settlement amount may be determined by settlement system 275.

Credit card server 280 may include one or more server devices, or other types of computation or communication devices, that gather, process, search, store, and/or provide information in a manner similar to that described herein. Credit card server 280 may authorize a credit card transaction based on a request to charge a purchase amount to a credit card associated with a customer. The request may be received, for example, from charging system 250. While credit card server 280 has been described in terms of a credit card transaction, credit card server 280 may correspond to any online payment system that processes online payment transactions. For example, credit card server 280 may process debit cards, electronic checks, bank wires, and/or may perform another type of electronic money transfer.

Although FIG. 2 shows example components of VPS 120, in other implementations, VPS 120 may include fewer components, different components, differently arranged components, or additional components than depicted in FIG. 2. Additionally or alternatively, one or more components of VPS 120 may perform functions described as being performed by one or more other components of VPS 120.

Figure 3:
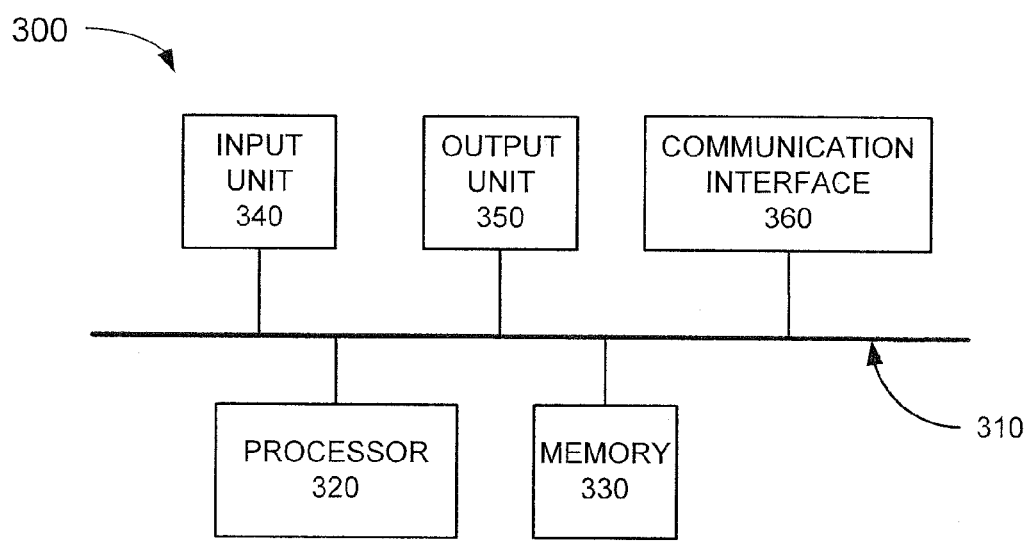
FIG. 3 is a diagram illustrating example components of a device that corresponds to one or more of the components of FIG. 2.

FIG. 3 is a diagram of example components of a device 300 that may correspond to user device 110, content provider 130, application server 210, IMG server 220, VOD server 225, CDN server 230, catalog server 235, VCM server 240, charging system 250, SSO server 255, profile server 260, ordering system 265, billing system 270, settlement system 275, and/or credit card server 280. Alternatively, each of user device 110, content provider 130, application server 210, IMG server 220, VOD server 225, CDN server 230, catalog server 235, VCM server 240, charging system 250, SSO server 255, profile server 260, ordering system 265, billing system 270, settlement system 275, and/or credit card server 280 may include one or more devices 300.

As shown in FIG. 3, device 300 may include a bus 310, a processor 320, a memory 330, an input unit 340, an output unit 350, and a communication interface 360. Bus 310 may include a path that permits communication among the components of device 300. Processor 320 may include a single-core processor, multi-core processor, microprocessor, and/or processing logic that may interpret and execute instructions. Memory 330 may include any type of dynamic storage device that may store information and instructions, for execution by processor 320, and/or any type of non-volatile storage device that may store information for use by processor 320.

Input unit 340 may include a mechanism that permits a user to input information to device 300, such as a keyboard, a keypad, a button, a switch, etc. Output unit 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to billing for a video provisioning system. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, VPS 120 may include fewer components, different components, differently arranged components, or additional components than depicted in FIG. 3. Additionally or alternatively, one or more components of device 300 may perform functions described as being performed by one or more other components of device 300.

Figure 4:
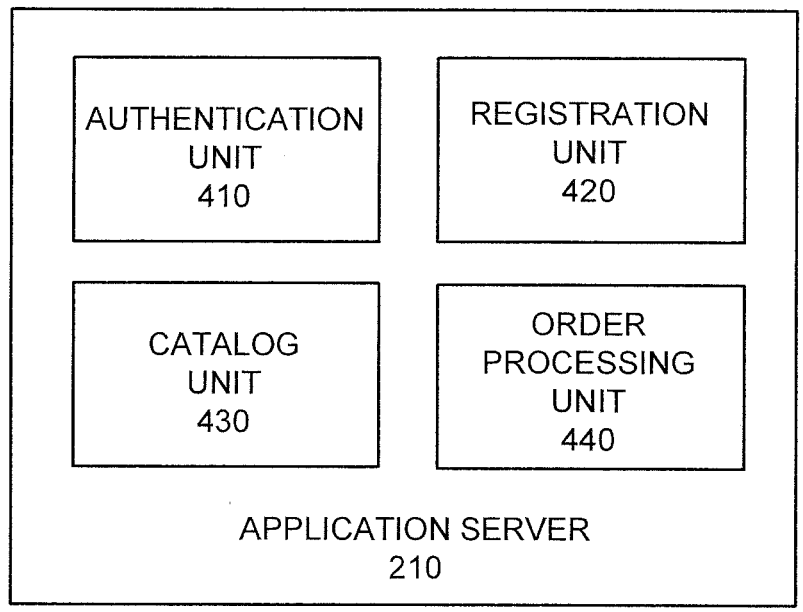
FIG. 4 is a diagram of example functional components of the application server of FIG. 2.

FIG. 4 is a diagram of example functional components of application server 210. As shown in FIG. 4, application server 210 may include an authentication unit 410, a registration unit 420, a catalog unit 430, and an order processing unit 440.

Authentication unit 410 may authenticate user device 110. For example, authentication unit 410 may present a login page and may receive a username and password from user device 110. As another example, authentication unit 410 may receive a username and password from a media manager application when user device 110 connects to application server 210 using the media manager application. Authentication unit 210 may forward the received username and password to SSO server 255 and may receive a confirmation from the SSO server 255 that the username and password are authentic.

Registration unit 420 may register a user device 110 with VPS 120. For example, a customer may not be associated with a bundled services account or a voice services account. Thus, when the customer requests to purchase a video asset through VPS 120, the customer may need to register with VPS 120 by generating a VPS profile. Registration unit 420 may interact with user device 110 to request information from the customer when the customer is to register with VPS 120. For example, registration unit 420 may request a customer to select a username and password and/or to select one or more user devices 110 to be associated with the VPS profile. Registration unit 420 may forward information received from the customer to profile server 260 along with a request to create a VPS profile based on the forwarded information.

Catalog unit 430 may interact with catalog server 235 to present information about available video assets to user device 110. For example, catalog unit 430 may receive video asset information from catalog server 430 and may format the information into a format compatible with application server 210. For example, catalog unit 430 may format the information into frames for a store front web page. As another example, catalog unit 430 may forward the information to IMG server 220, if the user device 110 communicating with application server 210 corresponds to a set top box.

Order processing unit 440 may process a request from user device 110 to purchase a video asset. For example, order processing unit 440 may receive a selection of a video asset, from the video assets presented as part of the catalog, along with a selection of a type of purchase of the video asset (e.g., buy, rent, subscription, etc.). Order processing unit 440 may contact profile server 260 to request information from the VPS profile associated with the customer and may receive information from the VPS profile from profile server 260, such as an account type associated with the customer (e.g., a bundled services account, a voice services account, or an online only account) and/or billing information associated with a particular account. Order processing unit 440 may forward the request to purchase the video asset, along with the information received from the VPS profile, to charging system 250. If order processing unit 440 receives an indication from profile server 260 that no VPS profile exists for the customer, order processing unit 440 may forward the request to purchase the video asset to charging system 250, along with a request to generate a VPS profile for the customer. The request to generate the VPS profile may include information identifying the customer (e.g., a username) and/or may include information identifying user device 110 that the customer used to access application server 210 (e.g., a set top box ID, a mobile communication device ID, etc.).

Although FIG. 4 shows example functional components of application server 210, in other implementations, application server 210 may include fewer functional components, different functional components, differently arranged functional components, or additional functional components than depicted in FIG. 4. Additionally or alternatively, one or more functional components of application server 210 may perform functions described as being performed by one or more other functional components of application server 210.

Figure 5:
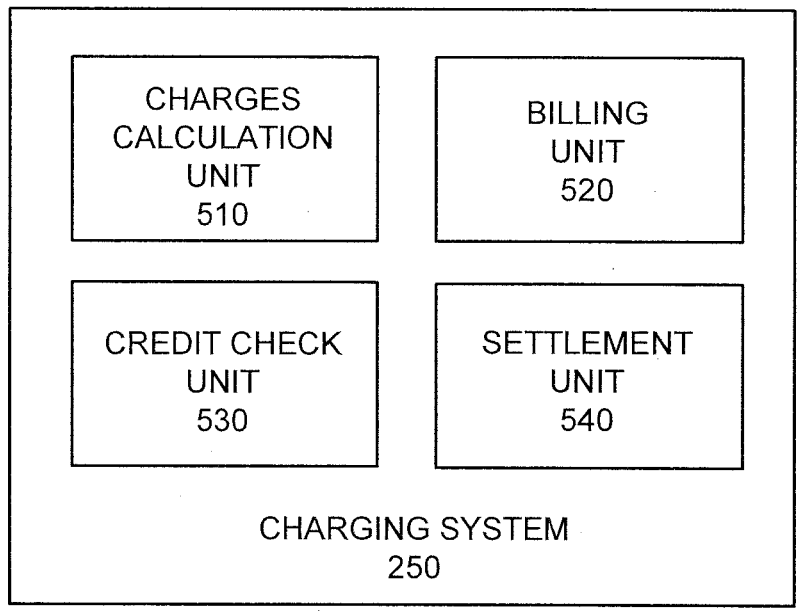
FIG. 5 is a diagram of example functional components of the charging system of FIG. 2.

FIG. 5 is a diagram of example functional components of charging system 250. As shown in FIG. 5, charging system 250 may include a charges calculation unit 510, a billing unit 520, a credit check unit 530, and a settlement unit 540.

Charges calculation unit 510 may compute charges for a purchase of a video asset. Charges calculation unit 510 may obtain information about the charges associated with the purchase from catalog server 235.

Billing unit 520 may identify an account to which charges computed for a purchase should be billed. For example, if the customer has an existing VPS profile, application server 210 may provide information about a billing account, retrieved from the VPS profile, to charging system 250 along with the purchase request. If the customer does not have an existing VPS profile, billing unit 520 may receive information identifying the customer, or information identifying user device 110, from application server 210 and may request billing information, associated with the customer, from ordering system 265. For example, billing unit 520 may receive a set top box ID from application server 210 and may request a billing account, associated with the set top box ID, from ordering system 265. As another example, billing unit 520 may receive a mobile communication device identifier from application server 210 and may request a billing account, associated with the mobile communication device identifier, from ordering system 265. As yet another example, billing unit 520 may receive a username from application server 210 and may request a billing account, associated with the username, from ordering system 265. Billing unit 520 may instruct billing system 270 to add the computed charges to a next bill associated with the determined billing account.

Additionally, billing unit 520 may provide the received billing account information to profile server 260, along with a request to generate a VPS profile for the customer. Furthermore, if billing unit 520 cannot identify an existing billing account, billing unit 520 may process a payment for the purchase using an online payment method. For example, billing unit 520 may obtain credit card information from user device 110 or from profile server 260 (if credit card information has been previously stored for the customer making the purchase). Billing unit 520 may request credit card server 280 to charge a credit card associated with the customer for the computed charges.

Credit check unit 530 may determine whether enough credit remains on the determined billing account to add the computed charges to the billing account. For example, credit check unit 530 may contact billing system 270 to determine whether the credit exits and may receive a confirmation from billing system 270. If billing system 270 informs credit check unit 530 that the billing account does not have enough credit, credit check unit 530 may inform billing unit 520 that there is not enough credit on the billing account to add the computed charges and billing unit 520 may request that the customer make an online payment for the computer charges.

Settlement unit 540 may determine a settlement payment for the purchase of the video asset based on an agreement with content provider 130 associated with the video asset. Settlement unit 540 may obtain information about the settlement payment associated with the purchase from catalog server 235. Settlement unit 540 may request settlement system 275 to process the settlement payment.

Although FIG. 5 shows example functional components of charging system 250, in other implementations, charging system 250 may include fewer functional components, different functional components, differently arranged functional components, or additional functional components than depicted in FIG. 5. Additionally or alternatively, one or more functional components of charging system 250 may perform functions described as being performed by one or more other functional components of charging system 250.

Figure 6A:
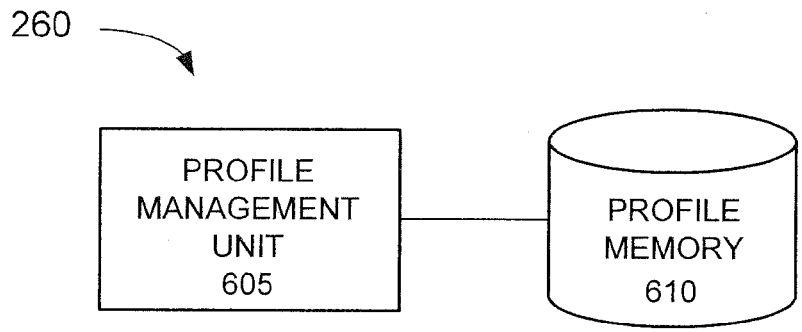
FIG. 6A is a diagram of example functional components of the profile server of FIG. 2.

FIG. 6A is a diagram of example functional components of profile server 260. As shown in FIG. 6A, profile server 260 may include a profile management unit 605 and a profile memory 610.

Profile management unit 605 may manage VPS profiles stored in profile memory 620. For example, profile management unit 605 may generate a VPS profile for a customer if a customer does not have a VPS profile and/or may update a VPS profile with new information. Profile management unit 605 may receive a request for information from a customer's profile and may retrieve the information from profile memory 610 and provide the information to application server 210.

Profile memory 610 may store VPS profiles associated with customers. Example information that may be stored in profile memory 610 is described below with reference to FIGS. 6B and 6C.

Although FIG. 6A shows example functional components of profile server 260, in other implementations, profile server 260 may include fewer functional components, different functional components, differently arranged functional components, or additional functional components than depicted in FIG. 6A. Additionally or alternatively, one or more functional components of profile server 260 may perform functions described as being performed by one or more other functional components of profile server 260.

Figure 6B:
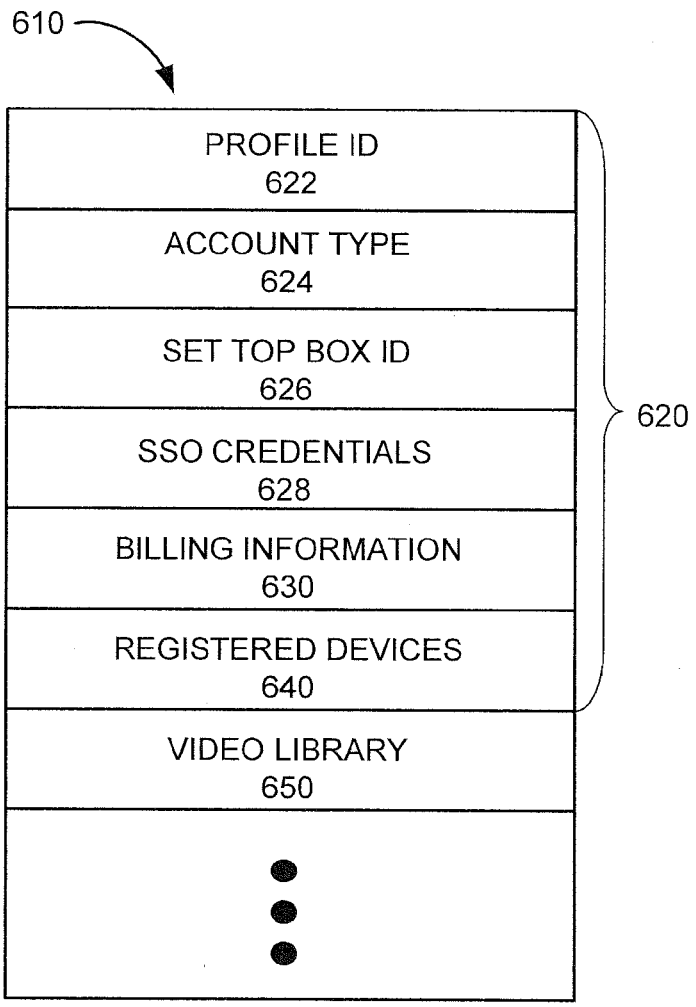

FIG. 6B is a diagram of example fields that may be stored in the profile memory 620 of FIG. 6A. In one example, profile memory 610 may be implemented in a storage device included as part of memory 330 of profile server 260. In another example, profile memory 610 may be implemented in another storage device associated with another device or group of devices separate from, and possibly remote from, profile server 260.

As shown in FIG. 6B, profile memory 610 may include one or more VPS profile records 620 (referred to herein collectively as "VPS profile records 620" and individually as "VPS profile record 620"). VPS profile record 620 may include a profile ID field 622, an account type field 624, a set top box ID field 626, an SSO credentials field 628, a billing information field 630, a registered devices field 640, and a video library 650.

Profile ID field 622 may include an identifier that uniquely identifies a VPS profile associated with a particular customer. Account type field 624 may identify an account type associated with the particular customer. For example, if the customer has a bundled services account, account type field 624 may identify the account type as a bundled services account. As another example, if the customer only has a voice services account, account type field 624 may identify the account type as a voice services account. As yet another example, if the customer has no bundled services account or other services account, (e.g., voice, television, and/or data) the customer may only be able to access VPS system via web portal store front associated with application server 210. Thus, account type field 624 may identify the account type as an "online only" account.

A set top box ID field 626 may include an identifier of a set top box associated with the customer. If the customer is not associated with a bundled services account, the customer may be not be associated with a set top box and set top box ID field 626 may be empty.

SSO credentials field 628 may store a username and password associated with the customer. If a customer accesses application server 210 using a media manager application or by logging in via a login page, profile server 260 may identify the VPS profile associated with the customer based on the username.

Billing information field 630 may identify a billing account associated with the customer. For example, if the customer is associated with a bundled services account, billing information field 630 may store information identifying a billing account (e.g., account number) associated with the bundled services account. As another example, if the customer is associated with a voice services account, billing information field 630 may store information identifying a billing account (e.g., account number) associated with the voice services account.

Registered device field 640 may store information identifying one or more user devices 110 registered with the customer's VPS account. The customer may register a particular number of user devices 110 with VPS system 110. Information associated with a registered device may include an identifier associated with the device and a type of user device. Types of user devices that may be registered may include, for example, a computer device (e.g., a personal computer, a lap top computer, a tablet computer, etc.), a mobile communication device (e.g., a Droid® device, a Blackberry® device, an iPhone® device, etc.), a set top box, a gaming device, and/or any other type of device capable of interacting with application server 120.

For example, if the user device type corresponds to a mobile communication device, the identifier may include a Mobile Subscriber Integrated Services Digital Network number (MSISDN), an International Mobile Subscriber Identity (IMSI) number, a mobile identification number (MIN), or an International Mobile Equipment Identifier (IMEI), an Integrated Circuit Card Identifier (ICCI), and/or any other mobile communication device identifier. Other examples of identifiers that may be included in association with a user device may include an Internet protocol (IP) address, a media access control (MAC) address, a compression/decompression (CODEC) identifier, and/or any other type of identifier.

Video library 650 may store information about video assets that have been purchased by the customer associated with the VPS profile. FIG. 6C is a diagram of example fields that may be stored in video library 650. As shown in FIG.

6C, video library 650 may include one or more video asset records (e.g., video asset record 660, video asset record 662, video asset record 664, etc.).

Each video asset record may include a user device field 642, a content field 644, a transaction field 646, a content marker 648, a catalog field 650, a parental controls field 652, and a global parental controls field 654.

User device field 642 may store information associated with the particular user device 110, such as a device identifier (e.g., an MDN, an IMSI, and MSISDN, a CODEC identifier, etc.), an address associated with user device 110 (e.g., a MAC address, an IP address), etc. Content field 644 may store information associated with a video asset, such as a content identifier, a title, etc., that is obtained and/or played by the particular user device 110. Transaction field 646 may store information identifying a type of purchase associated with the video asset, such as a buy transaction type, a rent transaction type, a subscription transaction type, or another type of transaction type. If the transaction type corresponds to a rent transaction type, transaction field 646 may store a rent period (e.g., 24 hours, 48 hours, etc.) associated with the rent transaction.

Content marker field 648 may store information regarding a bookmark, associated with the video asset identified in content field 644. The bookmark may identify a point, in the playing time of the video asset, at which the particular user device 110 stopped playing the video asset. Catalog field 650 may store information associated with a particular catalog (e.g., catalog server 235, IMG server 220, etc.) that stores metadata, associated with available video assets.

Parental controls field 635 may store information associated with parental controls, associated with the particular user device 110, that were specified by the user of the particular user device 110. The information associated with the parental controls may identify a content genre (e.g., horror, adult, etc.), a rating (e.g., restricted (R), mature audiences (MA), etc.), etc. that are not to be accessed, obtained, and/or played by the particular user device 110. Global parental controls field 640 may store information associated with parental controls that correspond to one or more different types of user devices 110 (e.g., a set top box, a computer device, a wireless handheld device, a gaming device, etc.) associated with the user of the particular user device 110.

Although FIGS. 6B and 6C shows example fields that may be stored in profile memory 610, in other implementations, profile memory 610 may include fewer fields, different fields, differently arranged fields, and/or additional fields than depicted in FIGS. 6B and 6C.

Figure 7:
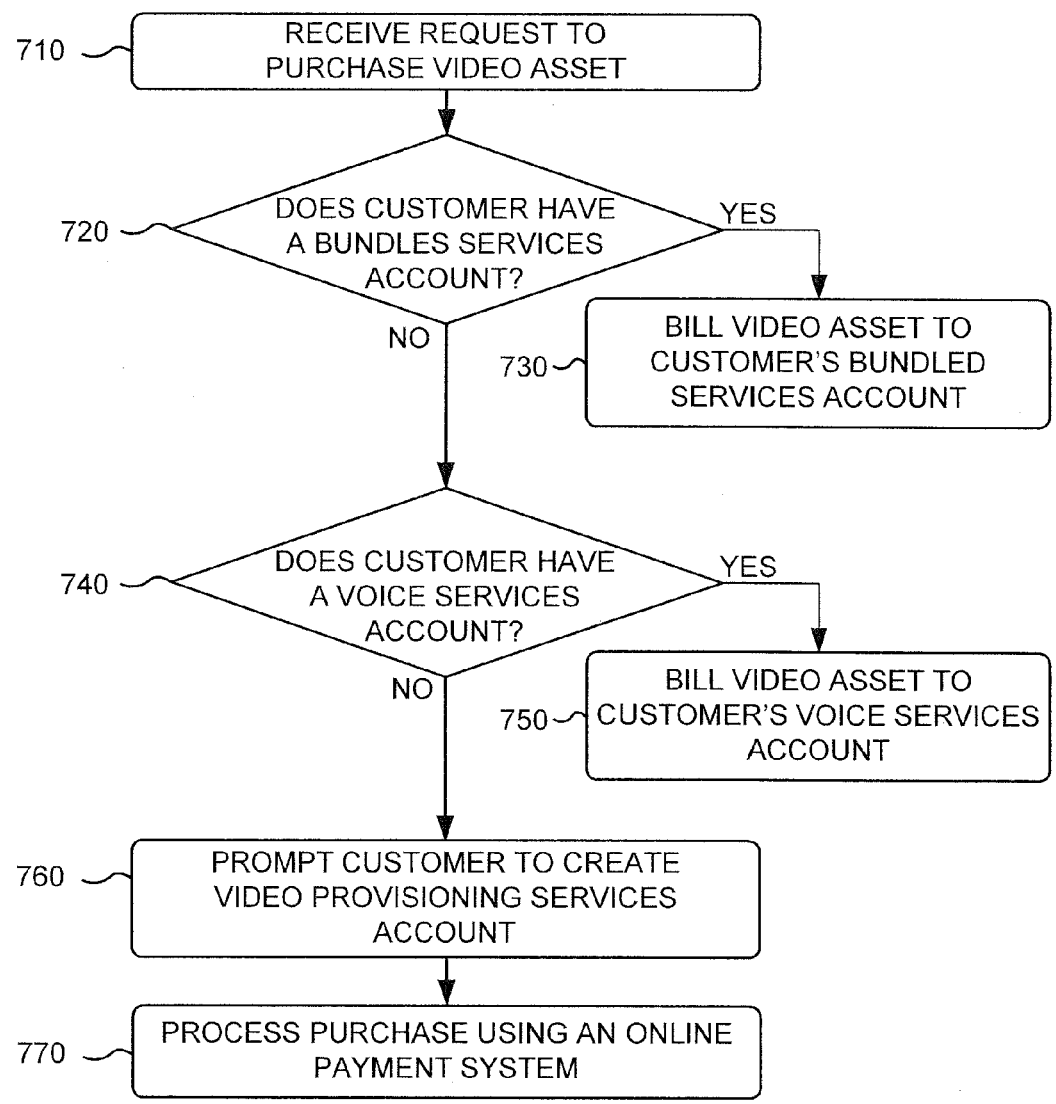
FIG. 7 is a flow chart of an example process for billing a customer for a purchase of video content according to an implementation described herein.

FIG. 7 is a flow chart of an example process for billing a customer for a purchase of a video asset according to an implementation described herein. In one implementation, the process of FIG. 7 may be performed by VPS 120. In other implementations, some or all of the process of FIG. 7 may be performed by another device or a group of devices separate from and/or possibly remote from VPS 120 and/or including VPS 120.

The process of FIG. 7 may include receiving a request to purchase a video asset (block 710). For example, application server 210 may receive a request from user device 110 to purchase a video asset. In one example, the request may be made by a set top box via IMG server 220.

In another example, the request may be made using a media manager application associated with VPS 120. The media manager application may be made available for download from a particular web site (e.g., from a web site associated with application server 210). The media manager application may allow a particular user device 110 to interact with VPS 120. Each particular type of user device may be associated with a particular media manager application. For example, a mobile communication device running on a Droid® operating system may be associated with a first media manager application, a personal computer running a Microsoft Windows® operating system may be associated with a second media manager application, etc. If the customer has a username, the media manager application may provide the username to application server 210.

In yet another example, the request may be made without a media manager application. For example, a customer may access a store front web page associated with application server 210, browse a catalog of video assets, and request to purchase a particular video asset. If the customer has a username, the customer may login in with the username.

A determination may be made as to whether the customer has a bundled services account (block 720). For example, application server 210 may determine whether the request was received from a set top box. If the request was received from a set top box, then the customer has a bundled services account. If the request was received from a user device 110 other than a set top box, application server 210 may determine whether the customer is associated with a VPS profile by sending the customer's username, or an identifier associated with user device 110, to profile server 260. If the username, or the identifier associated with user device 110, is associated with a VPS profile, account type field 624 of the VPS profile may identify an account type, which may correspond to a bundled services account. If the username, or the identifier associated with user device 110, is not associated with a VPS profile, application server 210 may forward information about the username, or the identifier associated with user device 110, to charging system 250 and charging system 250 may request ordering system 265 to determine whether the username, or the identifier associated with user device 110, is associated with a bundled services account. If the customer does not have a username, or if user device 110 cannot be identified, application server 210 may determine that the customer is not associated with a bundled services account.

If it is determined that the customer has a bundled services account (block 720—YES), the purchase of the video asset may be billed to the customer's bundled services account (block 730). For example, application server 210 may forward the purchase request to charging system 250. Charging system 250 may compute charges associated with the purchase and may instruct billing system 270 to add the computed charges to a next bill associated with the bundled services account.

If it is determined that the customer does not have a bundled services account (block 720—NO), a determination may be made as to whether the customer has a voice services account (block 740). For example, application server 210 may determine whether the customer is associated with a VPS profile by sending the customer's username, or an identifier associated with user device 110, to profile server 260. If the username, or the identifier associated with user device 110, is associated with a VPS profile, account type field 624 of the VPS profile may identify an account type, which may correspond to a voice services account. If the username, or the identifier associated with user device 110, is not associated with a VPS profile, application server 210 may forward information about the username, or the identifier associated with user device 110, to charging system 250 and charging system 250 may request ordering system 265 to determine whether the username, or the identifier associated with user device 110, is associated with a voice services account. If the customer does not have a username, or if user device 110 cannot be identified, application server 210 may determine that the customer is not associated with a voice services account.

If it is determined that the customer has a voice services account (block 740—YES), the purchase of the video asset may be billed to the customer's voice services account (block 750). For example, application server 210 may forward the purchase request to charging system 250. Charging system 250 may compute charges associated with the purchase and may instruct billing system 270 to add the computed charges to a next bill associated with the voice services account.

If it is determined that the customer does not have a voice services account (block 740—NO), the customer may be prompted to create a video provisioning services account (block 760). For example, application server 210 may provide registration instructions to user device 110. The user may enter requested registration information, such as a username and password, and application server 210 may instruct profile server 260 to generate a VPS profile for the customer. Application server 210 may provide information about the purchase request, along with information about the user's VPS profile, to charging system 250.

The purchase may be processed using an online payment system (block 770). For example, charging system 250 may request credit card information from user device 110. The user may enter the requested credit card information and user device 110 may send the credit card information to charging system 250. Charging system 250 may submit the charges and the credit card information to credit card server 280 and credit card server 280 may respond with an indication that the purchase has been approved.

FIGS. 8A-8E are flow charts of an example process for billing a customer for a purchase of a video asset according to an implementation described herein. In one implementation, the process of FIGS. 8A-8E may be performed by VPS 120. In other implementations, some or all of the process of FIGS. 8A-8E may be performed by another device or a group of devices separate from and/or possibly remote from VPS 120 and/or including VPS 120.

Figure 8A:
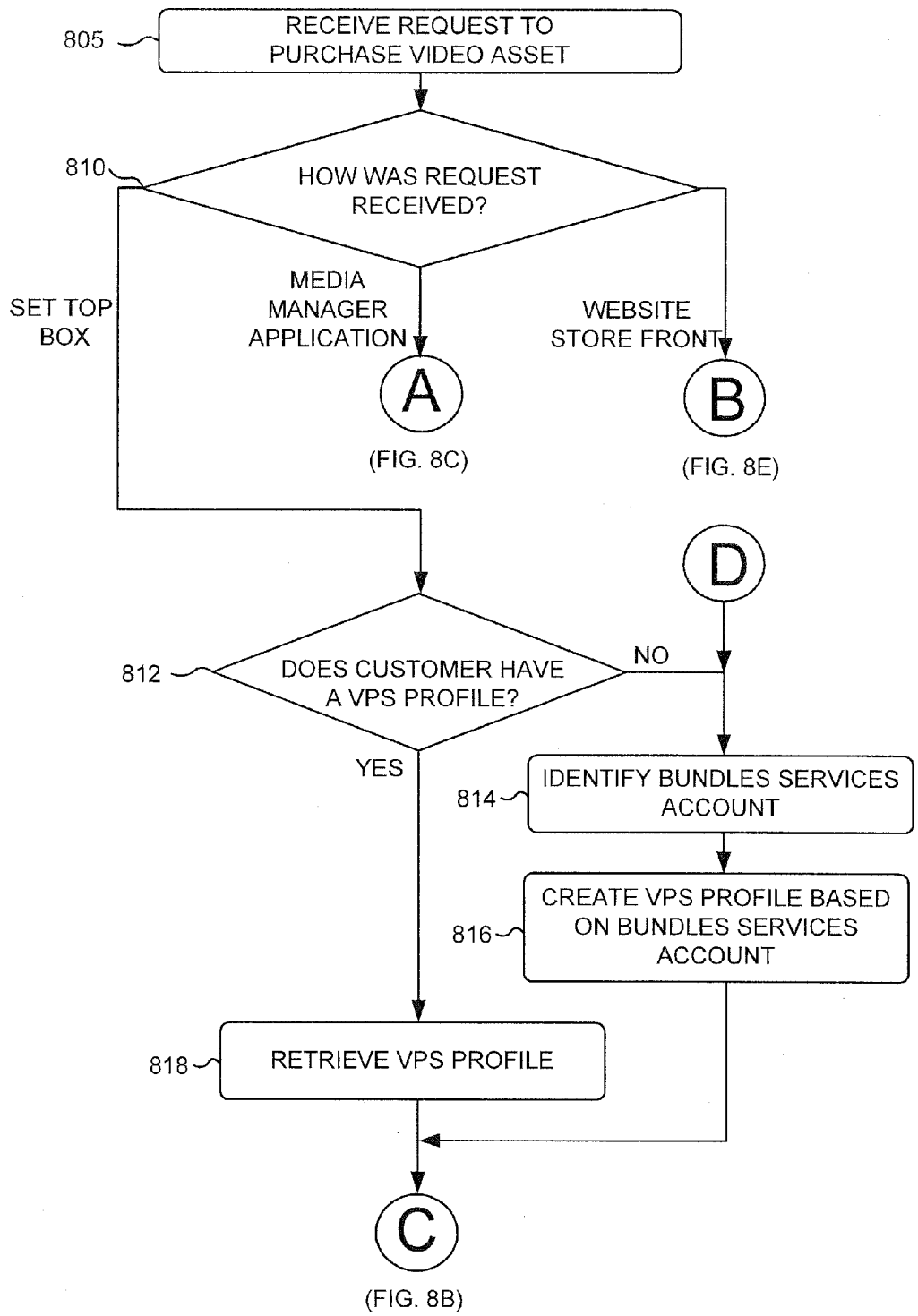
FIGS. 8A-8E are flow charts of an example process for billing a customer for a purchase of video content according to an implementation described herein.

The process of FIG. 8A may include receiving a request to purchase a video asset (block 805). For example, application server 210 may receive a request from user device 110 to purchase a video asset. A determination may be made as to how the request was received (block 810). For example, application server 210 may determine whether the request was received from a set top box, a media manager application, or via a website store front.

If it is determined that the request was received from a set top box (block 810—SET TOP BOX), a determination may be made as to whether the customer has a VPS profile (block 812). For example, application server 210 may determine whether the customer is associated with a VPS profile by sending an identifier associated with the set top box to profile server 260. Profile server 260 may access profile memory 610 and either provide information from the VPS profile to application server 210 or may send a response to application server 210, indicating that no VPS profile is associated with the set top box.

If it is determined that the customer does not have a VPS profile (block 812—NO), a bundle services account may be identified (block 814). For example, application server 210 may send a request to charging system 250 to generate a VPS profile for the customer. Charging system 250 may request bundle profile information from ordering system 265. The request may include an identifier associated with the set top box. Ordering system 265 may identify a bundle profile for the set top box and may provide information from the bundle profile to charging system 250. The provided information may include a billing account associated with the bundle profile. Charging system may provide the received bundle profile information to profile server 260 and profile server 260 may generate a VPS profile for the account associated with the set top box based on the received bundle profile information. The generated VPS profile may include the identifier associated with the set top box and an account type corresponding to a bundled services account type. Processing may continue to block 820 of FIG. 8B.

If it is determined that the customer does have a VPS profile (block 812—YES), the VPS profile may be retrieved (block 818). For example, profile server 260 may access profile memory 610 and provide information from the VPS profile to application server 210. The information may include information identifying a billing account associated with the bundled services profile associated with the customer.

Figure 8B:
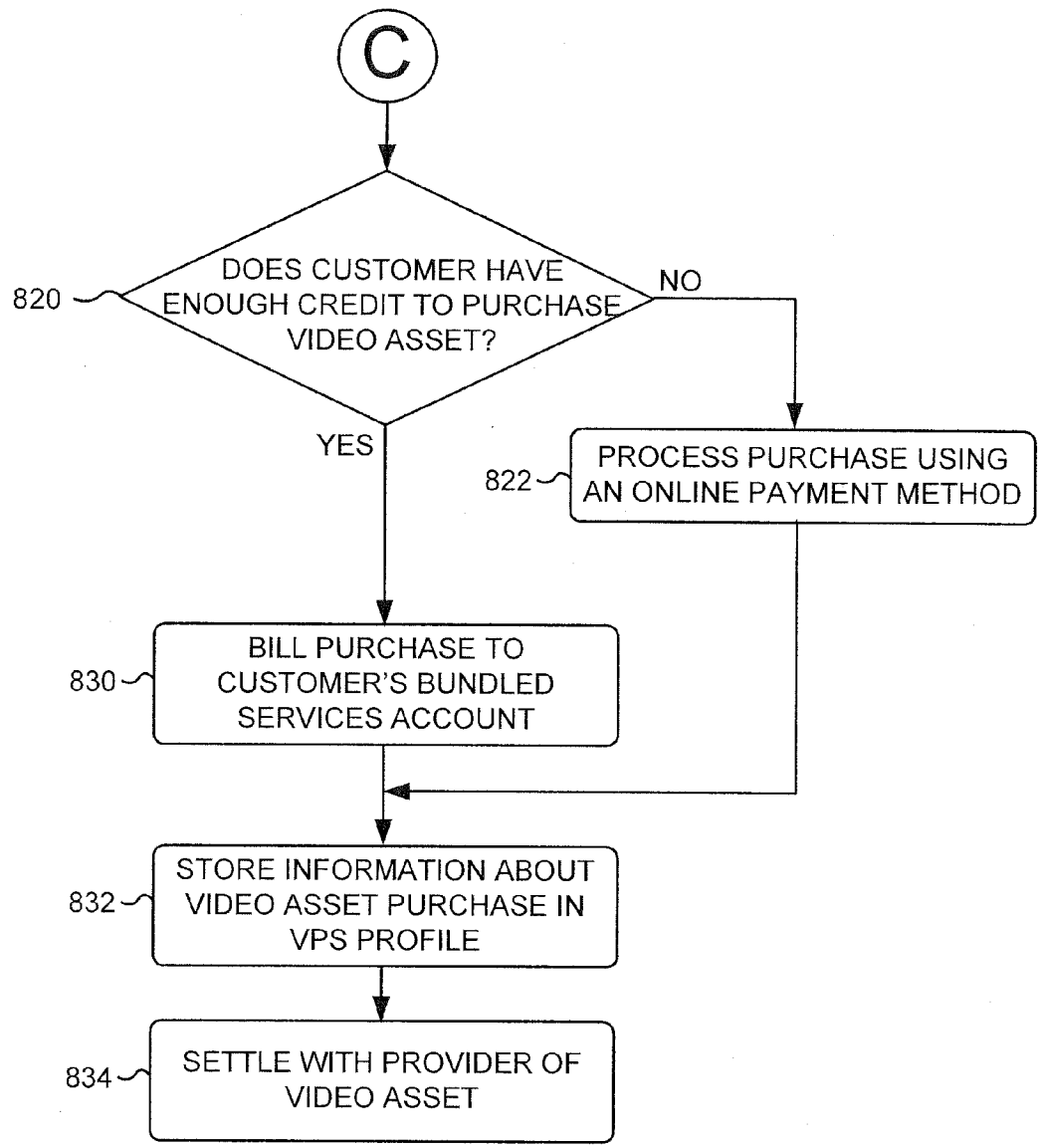

Continuing to FIG. 8B, a determination may be made as to whether the customer has enough credit to purchase the video asset (block 820). For example, charging system 250 may perform a credit check associated with the purchase by inquiring with billing system 270 as to whether the billing account associated with the customer's bundled services account has enough credit for the purchase of the video asset. Billing system 270 may respond with an indication of whether the billing account has enough credit for the purchase.

If it is determined that the customer does not have enough credit (block 820—NO), the purchase may be processed using an online payment method. For example, charging system 250 may request credit card information from the customer and may forward the credit card information to credit card server 280 to charge the purchase to the customer's credit card.

If it is determined that the customer does have enough credit (block 820—YES), the purchase may be billed to the customer's bundled services account. For example, charging system 270 may instruct billing system 270 to add the purchase to the next bill associated with the bundled services account. Thus, the customer may see the charges for the purchase of the video asset on the next bundled services bill.

Information about the video asset purchase may be stored in the customer's VPS profile (block 832). For example, charging system 250 may send information about the purchase to profile server 260 and profile server 260 may add the video asset to the library associated with the generated VPS account.

A provider of the video asset may be settled (block 834). For example, charging system 250 may further calculate a settlement payment associated with the purchase and may provide settlement payment information to settlement system 275. Settlement system 275 may settle a payment with content provider 130, associated with the purchased video asset, based on the received settlement information.

Figure 8C:
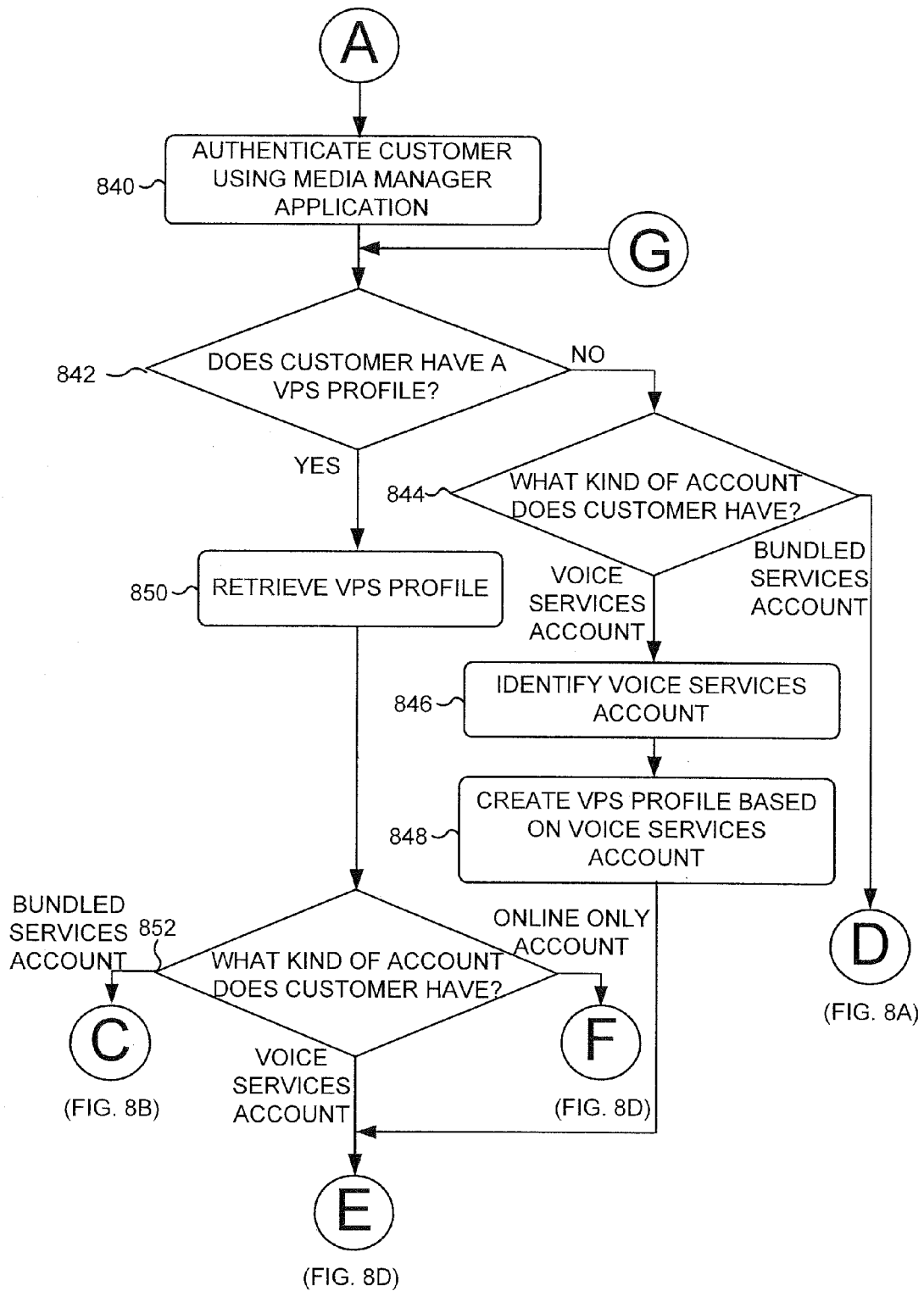

Returning to FIG. 8A, if it is determined that the request was received from a media manager application (block 810—MEDIA MANAGER APPLICATION), the customer may be authenticated using the media manager application (block 840, FIG. 8C). For example, when the user first activates the media manager application, the user may enter a username and password and the media manager application may store the username and password on user device 110. When the user subsequently activates the media manager application, the media manager application may submit the username and password to application serve 210. Application server 210 may attempt to authenticate the customer by sending the username and password to SSO server 225. Application server 210 may receive an authentication response from SSO server 255.

A determination may be made as to whether the customer has a VPS profile (block 842). For example, application server 210 may determine whether the customer is associated with a VPS profile by sending a username, or an identifier associated with user device 110 on which the media manager application was activated, to profile server 260. Profile server 260 may access profile memory 610 and either provide information from the VPS profile to application server 210 or may send a response to application server 210, indicating that no VPS profile is associated with the customer.

If it is determined that the customer does not have a VPS profile (block 842—NO), a determination may be made as to what kind of account the customer may have (block 844). The customer may have a bundled services profile or a voice services profile. If the customer requested a purchase using media manager application and the customer does not have a VPS profile, it may be unlikely that the customer has an "online only" account, since in order for the customer to download the media manager application, the customer may have needed to register with VPS 120. However, if the customer has a bundled services profile or a voice services profile, the customer may be able to authenticate with application server 210 using an existing username, and thus the customer may be able to download the media manager application without having a VPS profile.

The determination as to whether the customer has a bundled services account or a voice services account may be made by charging system 250. For example, application server 210 may send a username, or an identifier associated with user device 110, to charging system 250 along with a request to generate a VPS profile. Charging system 250 may request information about the username, or the identifier associated with user device 110, from ordering system 265.

If it is determined that the customer has a bundled services account (block 844—BUNDLED SERVICES ACCOUNT), processing may return to block 814 of FIG. 8A. If it is determined that the customer has a voice services account (block 844—VOICE SERVICES ACCOUNT), a voice services account may be identified (block 846). For example, charging system 250 may receive information about the voice services account from ordering system 265.

A VPS profile may be created based on the voice services account (block 848). For example, charging system 250 may send a request to profile server 260 to create a VPS profile based on the voice services account. The generated VPS profile may include an identifier associated with user device 110, an account type corresponding to a voice services account, and SSO credentials (e.g., username and password) associated with the account, and billing information associated with the voice services account. Processing may continue to block 860 of FIG. 8D.

If it is determined that the customer has a VPS profile (block 842—YES), the VPS profile may be retrieved (block 850). For example, application server 210 may receive information from the VPS profile from profile server 260. The information may include an account type associated with the customer.

A determination may be made as to what kind of account the customer has (block 852). For example, application server 210 may provide an account type to charging system 250 along with the purchase request. The account type may correspond to a bundles services account type, a voice services account type, or an "online only" account type.

If it is determined that the customer has a bundled services account (block 852—BUNDLED SERVICES ACCOUNT), processing may continue to block 820 of FIG. 8B. If it is determined that the customer has a voice services account (block 852—VOICE SERVICES ACCOUNT), processing may continue to block 860 of FIG. 8D. If it is determined that the customer has an "online only" account, processing may continue to block 862 of FIG. 8D.

Figure 8D:
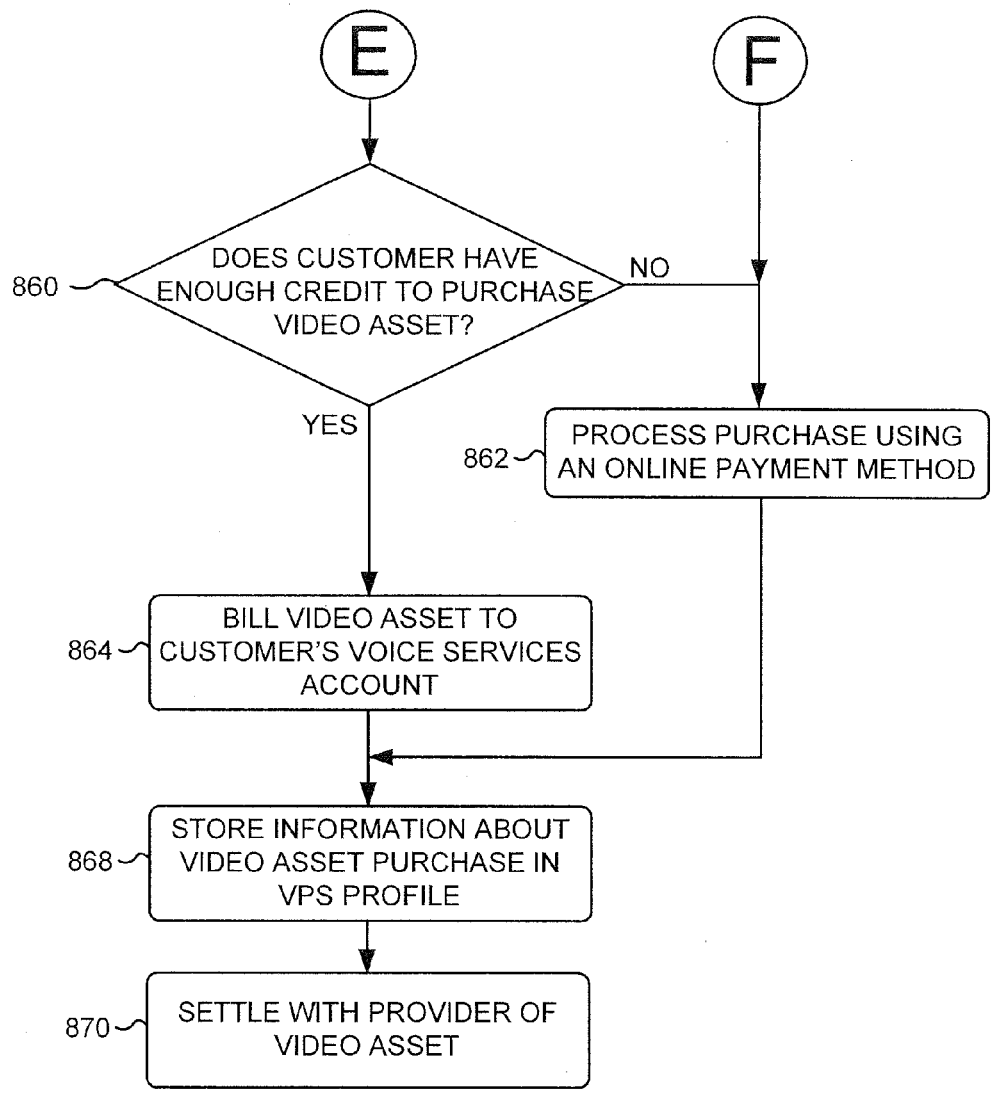

Continuing at FIG. 8D, a determination may be made as to whether the customer has enough credit to purchase the video asset (block 860). For example, charging system 250 may perform a credit check associated with the purchase by inquiring with billing system 270 as to whether the billing account associated with the customer's voice services account has enough credit for the purchase of the video asset. Billing system 270 may respond with an indication of whether the billing account has enough credit for the purchase.

If it is determined that the customer does not have enough credit (block 860—NO), the purchase may be processed using an online payment method. For example, charging system 250 may request credit card information from the customer and may forward the credit card information to credit card server 280 to charge the purchase to the customer's credit card.

If it is determined that the customer does have enough credit (block 860—YES), the purchase may be billed to the customer's voice services account. For example, charging system 270 may instruct billing system 270 to add the purchase to the next bill associated with the voice services account. Thus, the customer may see the charges for the purchase of the video asset on the next telephone bill.

Information about the video asset purchase may be stored in the customer's VPS profile (block 868). For example, charging system 250 may send information about the purchase to profile server 260 and profile server 260 may add the video asset to the library associated with the generated VPS account. A provider of the video asset may be settled (block 870). For example, charging system 250 may further calculate a settlement payment associated with the purchase and may provide settlement payment information to settlement system 275. Settlement system 275 may settle a payment with content provider 130, associated with the purchased video asset, based on the received settlement information.

Figure 8E:
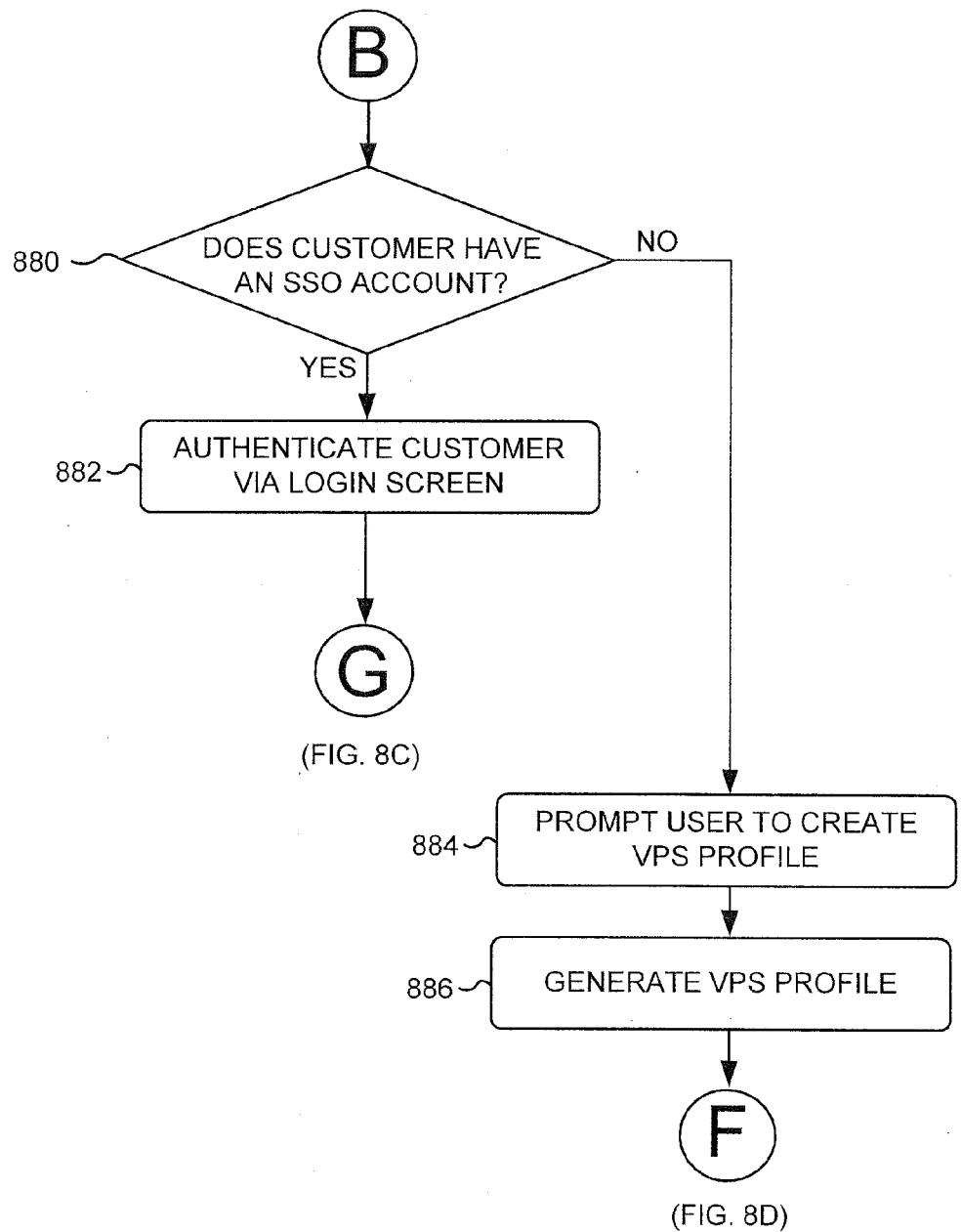

Returning to FIG. 8A, if it is determined that the request was received via a website store front (block 810—WEBSITE STORE FRONT), processing may continue to FIG. 8E. For example, the customer may browse a catalog of video assets by accessing a web page associated with application server 210. A determination may be made as to whether the customer has an SSO account (block 880). For example, application server 210 may, upon the customer requesting to purchase a video asset, present a login screen. If the customer has a username and password, the customer may log in via the login screen.

If it is determined that the customer has an SSO account (block 880—YES), the customer may be authenticated via the login screen (block 882). For example, application server 210 may receive a username and password from user device 110, forward the username and password to SSO server 255, and may receive a confirmation from SSO server 255 that the customer has been authenticated. Processing may continue to block 842 of FIG. 8C.

If it is determined that the customer does not have an SSO account (block 880—NO), the customer may be prompted to create a VPS profile. For example, if the customer does not have a username and password, VPS 120 may not have any associated account in connection with the customer and may have no way of determining who the customer is. Application server 210 may present a registration screen to user device 110 along with a request to provide particular information. The user may be prompted to select a username and password. The user may also be prompted to register one or more devices with VPS 120. A VPS profile may be generated (block 886). For example, application server 120 may instruct profile server 260 to generate a VPS profile for the customer. The VPS profile may be designated as an "online only" account. Processing may return to block 862 of FIG. 8D.

While not shown in FIGS. 8A-8E, VPS 120 may enable a user to continue to be able to access any purchased video assets even if the customer cancels an existing account that has been used to purchase video assets. For example, the customer may cancel an existing bundled services account or an existing voice services account. In that case, the customer's VPS profile may be modified by changing the account type to an "online only" account. Thus, for example, if the customer cancels a bundled services account and returns a set top box associated with the bundled services account, the customer may continue to be able to access the customer's VPS profile using a media manager application and may continue to consume any purchased video assets. Additionally, the customer may continue to purchase additional video assets using a media manager application or by accessing the website store frontstore front.

Figure 9:
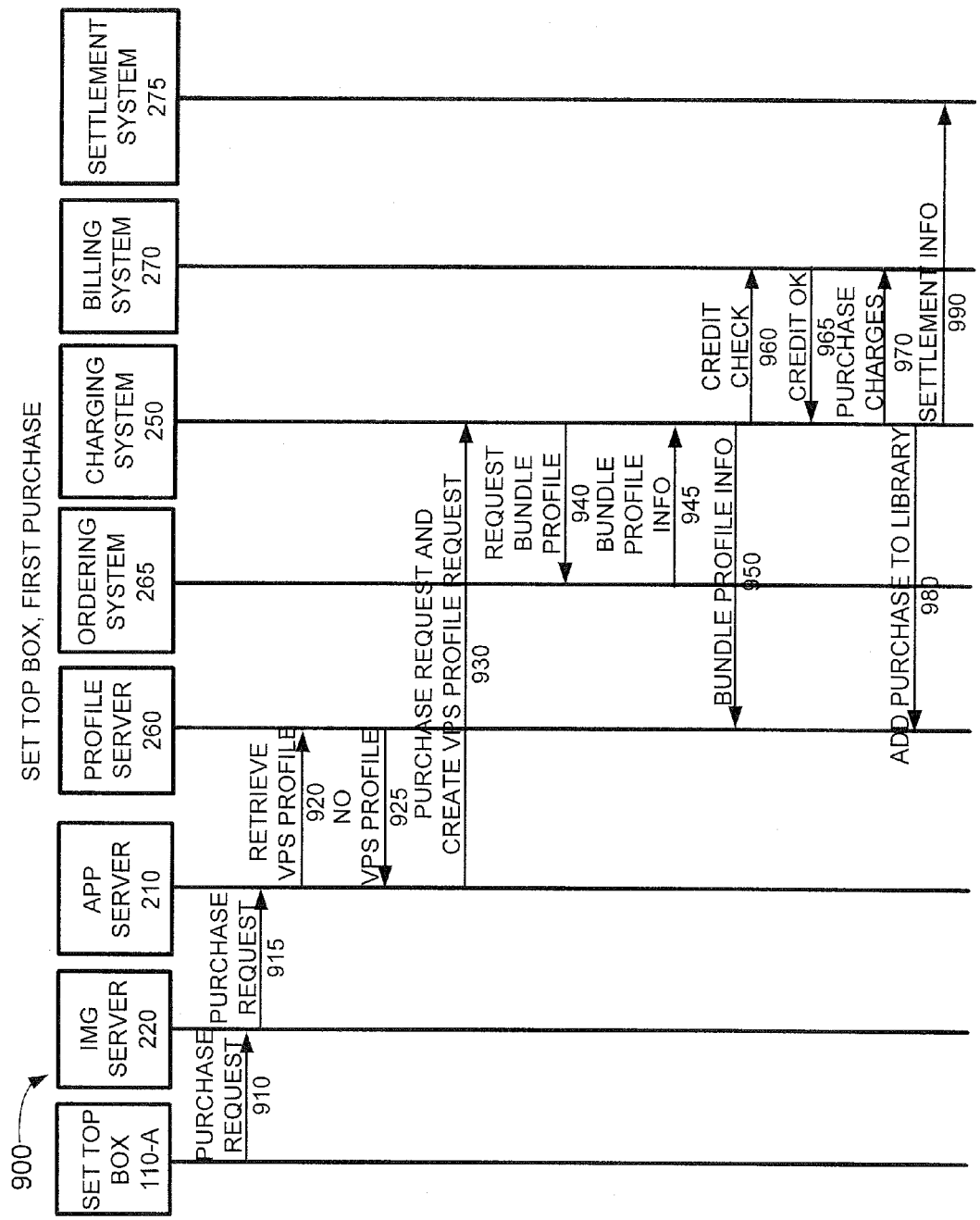
FIG. 9 is a diagram of an example signal flow of a first purchase of video content using a set top box according to an implementation described herein.

FIG. 9 is a diagram of an example signal flow 900 of a first purchase of a video asset using a set top box according to an implementation described herein. As shown in FIG. 9, example signal flow 900 may include set top box 110-A sending a purchase request to IMG server 220 (signal 910). For example, a user may access a menu stored at IMG server 220 via set top box 110-A and may select to purchase a movie from a menu. IMG server 220 may forward the purchase request to application server 210 (signal 915).

Application server 210 may request a VPS profile from profile server 260 (signal 920). The request may include an identifier associated with set top box 110-A. Profile server 260 may access profile memory 610 and determine that no VPS profile exists that is associated with set top box 110-A. Profile server 260 may send a response to application server 210, indicating that no VPS profile is associated with set top box 110-A (signal 925).

In response to determining that no VPS profile exists for the set top box 110-A, application server 210 may send a request to charging system 250 (signal 930). The request may include information about the purchase, including information identifying the movie and that the type of purchase was a buy purchase of the movie. Additionally, the request may include a request to generate a VPS profile for set top box 110-A.

Charging system 250 may compute charges for the purchase. Charging system 250 may obtain information from catalog server 235 during computation of the charges (not shown in FIG. 9). Additionally, charging system 250 may request bundle profile information from ordering system 265 (signal 940). The request may include information identifying set top box 110-A. Ordering system 265 may identify a bundle profile for set top box 110-A and may provide information from the bundle profile to charging system 250 (signal 945). The provided information may include a billing account associated with the bundle profile and SSO credentials associated with the bundle profile.

Charging system may provide the received bundle profile information to profile server 260 (signal 950). Profile server 260 may generate a VPS profile for the account associated with set top box 110-A based on the received bundle profile information. The generated VPS profile may include an ID associated with set top box 110-A, an account type (a bundled services account), and SSO credentials associated with the account.

Charging system 250 may perform a credit check associated with the purchase by inquiring with billing system 270 as to whether the billing account associated with set top box 110-A has enough credit for the purchase of the video asset (signal 960). Billing system 270 may respond with an indication that the billing account has enough credit for the purchase (signal 965). In response, charging system 270 may instruct billing system 270 to add the purchase to the next bill associated with the billing account associated with set top box 110-A (signal 970). Thus, the customer may see the charges for the purchase of the video asset on the next bundled services bill.

If, on the other hand, billing system 270 were to respond with an indication that the billing account does not have enough credit for the purchase (e.g., the customer is delinquent on the account, where the delinquent amount is greater than a particular threshold amount), then charging system 250 may not add the purchase to the next bill associated with the billing account associated with set top box 110-A. Rather, charging system 250 may request immediate payment for the purchase using an online payment method. For example, charging system 250 may send a request application server 210 to request credit card information from set top box 110-A.

Charging system 250 may further send information about the purchase to profile server 260 (signal 980). Profile server 260 may add the video asset to the library associated with the generated VPS account. Charging system 250 may further calculate a settlement payment associated with the purchase and may provide settlement payment information to settlement system 275 (signal 990). Settlement system 275 may settle a payment with content provider 130, associated with the purchased video asset, based on the received settlement information.

Figure 10:
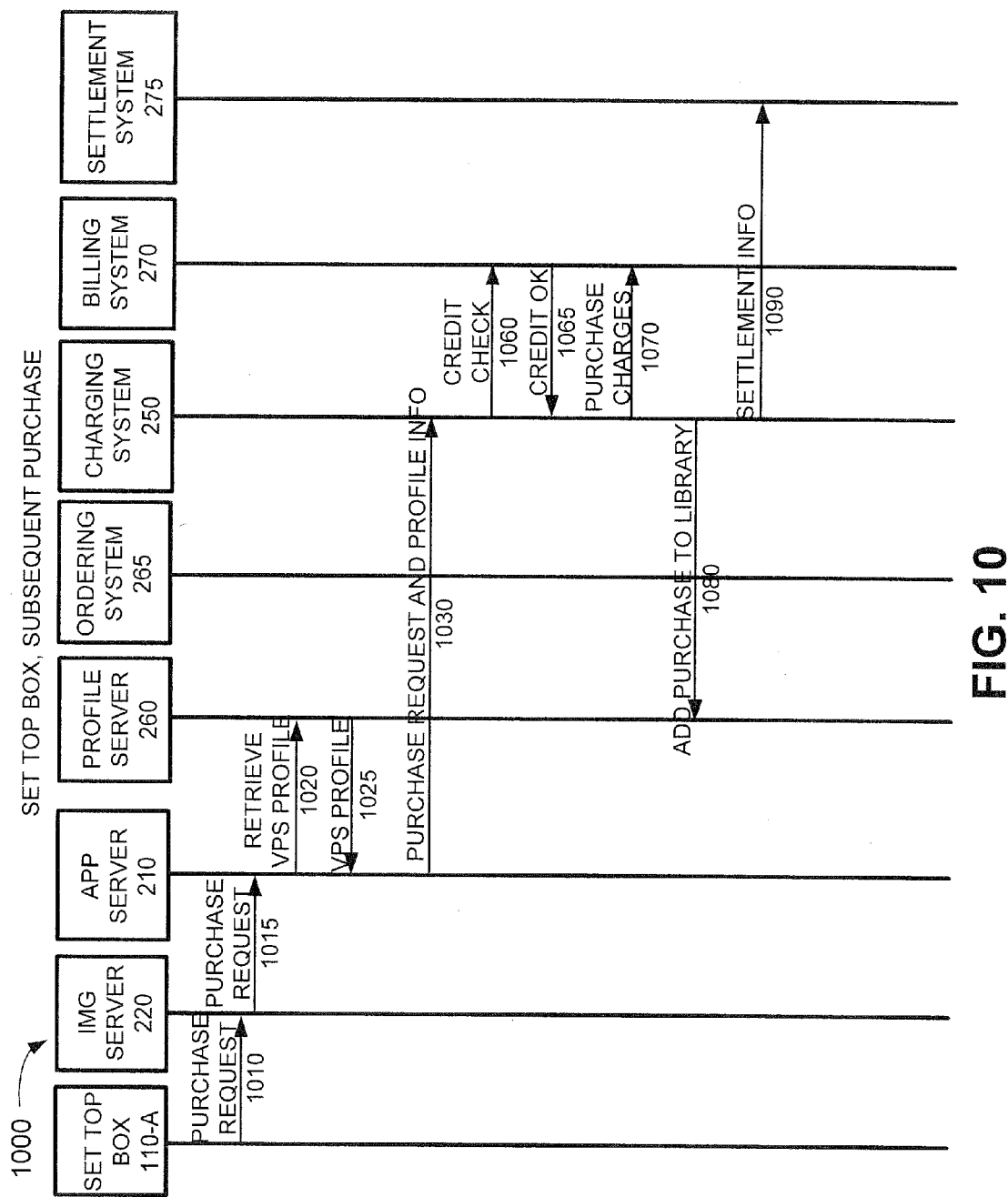
FIG. 10 is a diagram of an example signal flow of a subsequent purchase of video content using a set top box according to an implementation described herein.

FIG. 10 is a diagram of an example signal flow 1000 of a subsequent purchase of a video asset using a set top box according to an implementation described herein. As shown in FIG. 10, example signal flow 1000 may include set top box 110-A sending a purchase request to IMG server 220 (signal 1010). For example, a user may access a menu stored at IMG server 220 via set top box 110-A and may select to rent a movie for 24 hours. IMG server 220 may forward the purchase request to application server 210 (signal 1015).

Application server 210 may request a VPS profile from profile server 260 (signal 1020). The request may include an identifier associated with set top box 110-A. Since the customer has made a previous purchase of a video asset using VPS system 120, a VPS profile has been previously created for the customer. Thus, profile server 260 may access profile memory 610, may identify a VPS profile associated with set top box 110-A, and may provide information from the VPS profile to application server 210 (signal 1025). The information may include, for example, information identifying a bundled services billing account associated with set top box 110-A.

In response to receiving information from the VPS profile, application server 210 may send a request to charging system 250 (signal 1030). The request may include information about the purchase, including information identifying the movie and that the type of purchase was a 24 hour rental of the movie. Additionally, the request may include information identifying a bundled services billing account associated with set top box 110-A.

Charging system 250 may compute charges for the purchase. Charging system 250 may obtain information from catalog server 235 during computation of the charges (not shown in FIG. 10). Charging system 250 may further perform a credit check associated with the purchase by inquiring with billing system 270 as to whether the billing account associated with set top box 110-A has enough credit for the purchase of the video asset (signal 1060). Billing system 270 may respond with an indication that the billing account has enough credit for the purchase (signal 1065). In response, charging system 270 may instruct billing system 270 to add the purchase to the next bill associated with the billing account associated with set top box 110-A (signal 1070). Thus, the customer may see the charges for the purchase of the video asset on the next bundled services bill.

Charging system 250 may further send information about the purchase to profile server 260 (signal 1080). Profile server 260 may add the video asset to the library associated with the generated VPS account. The since the purchase was a 24 hour rental of the movie, the transaction type for the video asset record may indicate that the user's access to the video asset expires in 24 hours. Charging system 250 may further calculate a settlement payment associated with the purchase and may provide settlement payment information to settlement system 275 (signal 1090). Settlement system 275 may settle a payment with content provider 130, associated with the purchased video asset, based on the received settlement information.

Figure 11:
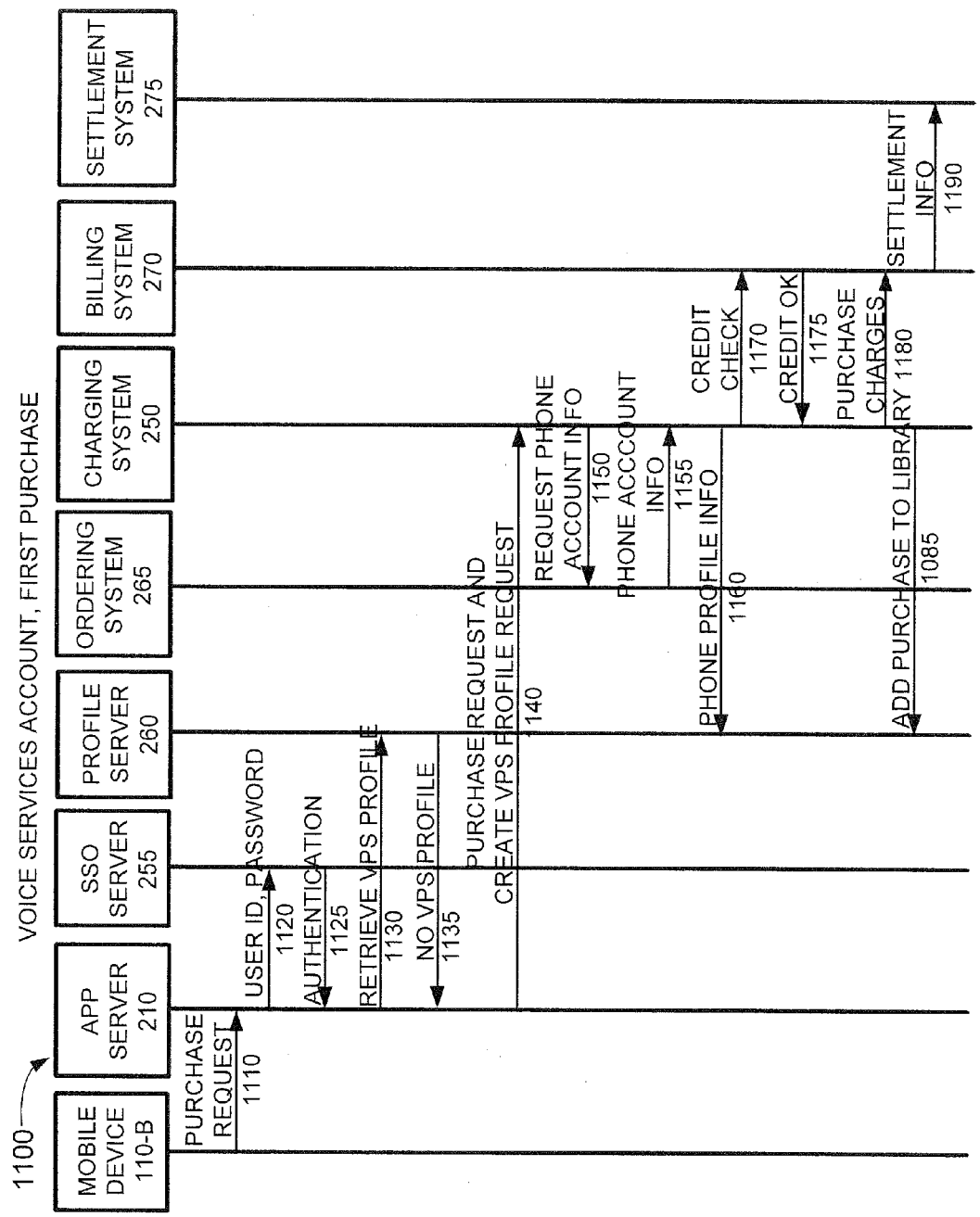
FIG. 11 is a diagram of an example signal flow of a first purchase of video content using a wireless mobile device according to an implementation described herein.

FIG. 11 is a diagram of an example signal flow 1100 of a first purchase of a video asset using a wireless mobile device according to an implementation described herein. As shown in FIG. 11, example signal flow 1100 may include mobile device 110-B sending a purchase request to application server 210 (signal 1110). For example, a user may download a media manager application to mobile device 110-B. The media manager application may allow the user to interact with VPS 120 via mobile device 110-B by browsing a catalog of available video assets, purchasing a video asset, and/or consuming the purchased video asset. The user may activate the media manager application and request to purchase a video asset using the media manager application. For example, the user may request to buy a movie.

Application server 210 may receive the purchase request from mobile device 110-B and may attempt to authenticate mobile device 110-B by sending credentials associated with mobile device 110-B to SSO server 225 (signal 1120). For example, mobile device 110-B may submit a username and password along with the purchase request. The user associated with mobile device 110-B may have SSO credentials because the user may have an existing wireless call plan account, associated with mobile device 110-B, which may have allowed the user to download the media manager application.

Application server 210 may receive an authentication response from SSO server 255 (signal 1125). Application server 210 may subsequently request a VPS profile from profile server 260 (signal 1130). The request may include the SSO credentials associated with mobile device 110-B. Profile server 260 may access profile memory 610 and determine that no VPS profile exists that is associated with mobile device 110-B. Profile server 260 may send a response to application server 210, indicating that no VPS profile is associated with mobile device 110-B (signal 1135).

In response to determining that no VPS profile exists for mobile device 110-B, application server 210 may send a request to charging system 250 (signal 1150). The request may include information about the purchase, including information identifying the movie and that the type of purchase was a buy purchase of the movie. Additionally, the request may include a request to generate a VPS profile for mobile device 110-B.

Charging system 250 may compute charges for the purchase. Charging system 250 may obtain information from catalog server 235 during computation of the charges (not shown in FIG. 11). Additionally, charging system 250 may request voice profile information from ordering system 265 (signal 1140). The request may include information identifying mobile device 110-B. Ordering system 265 may identify a phone account associated with mobile device 110-B and may provide information from the phone account to charging system 250 (signal 1155). The provided information may include a billing account associated with the phone account.

Charging system may provide the received phone account information to profile server 260 (signal 1160). Profile server 260 may generate a VPS profile for the account associated with mobile device 110-B based on the received phone account information. The generated VPS profile may include an identifier associated with mobile device 110-B, an account type (a voice services account), and SSO credentials associated with the account.

Charging system 250 may perform a credit check associated with the purchase by inquiring with billing system 270 as to whether the billing account associated with mobile device 110-B has enough credit for the purchase of the video asset (signal 1170). Billing system 270 may respond with an indication that the billing account has enough credit for the purchase (signal 1175). In response, charging system 270 may instruct billing system 270 to add the purchase to the next bill associated with the billing account associated with mobile device 110-B (signal 1180). Thus, the customer may see the charges for the purchase of the video asset on the next phone bill.

Charging system 250 may further send information about the purchase to profile server 260 (signal 1185). Profile server 260 may add the video asset to the library associated with the generated VPS account. Charging system 250 may further calculate a settlement payment associated with the purchase and may provide settlement payment information to settlement system 275 (signal 1190). Settlement system 275 may settle a payment with content provider 130, associated with the purchased video asset, based on the received settlement information.

Figure 12:
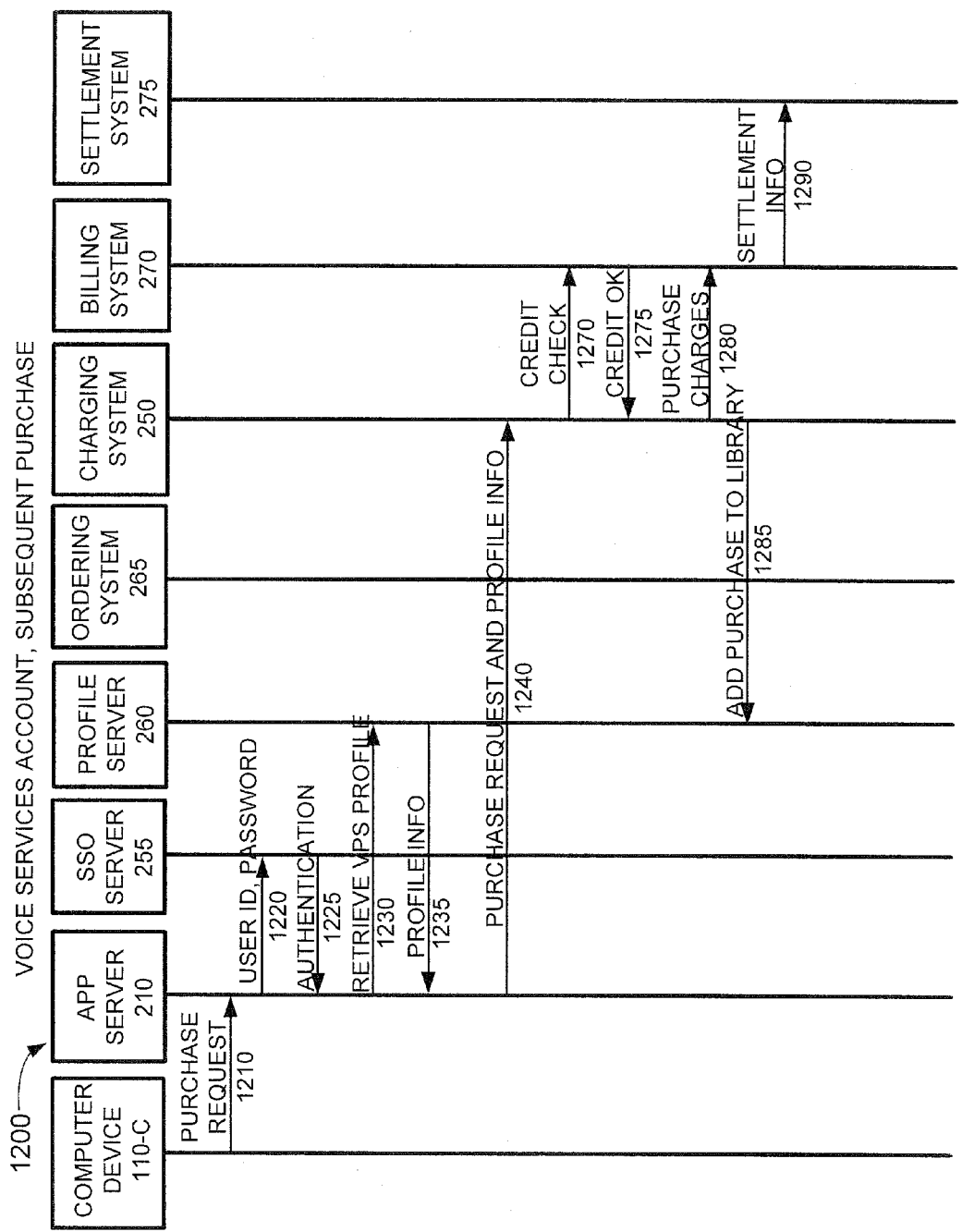
FIG. 12 is a diagram of an example signal flow of a subsequent purchase of video content using a wireless mobile device according to an implementation described herein.

FIG. 12 is a diagram of an example signal flow 1200 of a subsequent purchase of video content using a wireless mobile device according to an implementation described herein. As shown in FIG. 12, example signal flow 1200 may include computer device 110-C sending a purchase request to application server using the media manager application (signal 1210). For example, the user associated with mobile device 110-B may download the media manager application to the user's computer device 110-C and may request to purchase another movie via VPS 120. Application server 210 may receive the purchase request from computer device 110-C and may attempt to authenticate computer device 110-C by sending credentials associated with computer device 110-C to SSO server 225 (signal 1220). For example, computer device 110-C may submit the username and password along with the purchase request.

Application server 210 may receive an authentication response from SSO server 255 (signal 1225). Application server 210 may subsequently request a VPS profile from profile server 260 (signal 1230). The request may include the SSO credentials associated with computer device 110-C. Since the customer has made a previous purchase of a video asset using VPS system 120, a VPS profile has been previously created for the customer. Thus, profile server 260 may access profile memory 610, may identify a VPS profile associated with computer device 110-C based on the provided SSO credentials, and may provide information from the VPS profile to application server 210 (signal 1235). The information may include, for example, information identifying a telephone billing account associated with the VPS account (and associated with mobile device 110-B).

In response to receiving information from the VPS profile, application server 210 may send a request to charging system 250 (signal 1240). The request may include information about the purchase, including information identifying the movie and that the type of purchase was a 24 hour rental of the movie. Additionally, the request may include information identifying a telephone billing account associated with mobile device 110-B.

Charging system 250 may compute charges for the purchase. Charging system 250 may obtain information from catalog server 235 during computation of the charges (not shown in FIG. 12). Charging system 250 may further perform a credit check associated with the purchase by inquiring with billing system 270 as to whether the billing account associated with mobile device 110-B has enough credit for the purchase of the video asset (signal 1270). Billing system 270 may respond with an indication that the billing account has enough credit for the purchase (signal 1275). In response, charging system 270 may instruct billing system 270 to add the purchase to the next bill associated with the billing account associated with mobile device 110-B (signal 1280). Thus, the customer may see the charges for the purchase of the video asset on the next telephone bill.

Charging system 250 may further send information about the purchase to profile server 260 (signal 1285). Profile server 260 may add the video asset to the library associated with the generated VPS account. Charging system 250 may further calculate a settlement payment associated with the purchase and may provide settlement payment information to settlement system 275 (signal 1290). Settlement system 275 may settle a payment with content provider 130, associated with the purchased video asset, based on the received settlement information.

Figure 13:
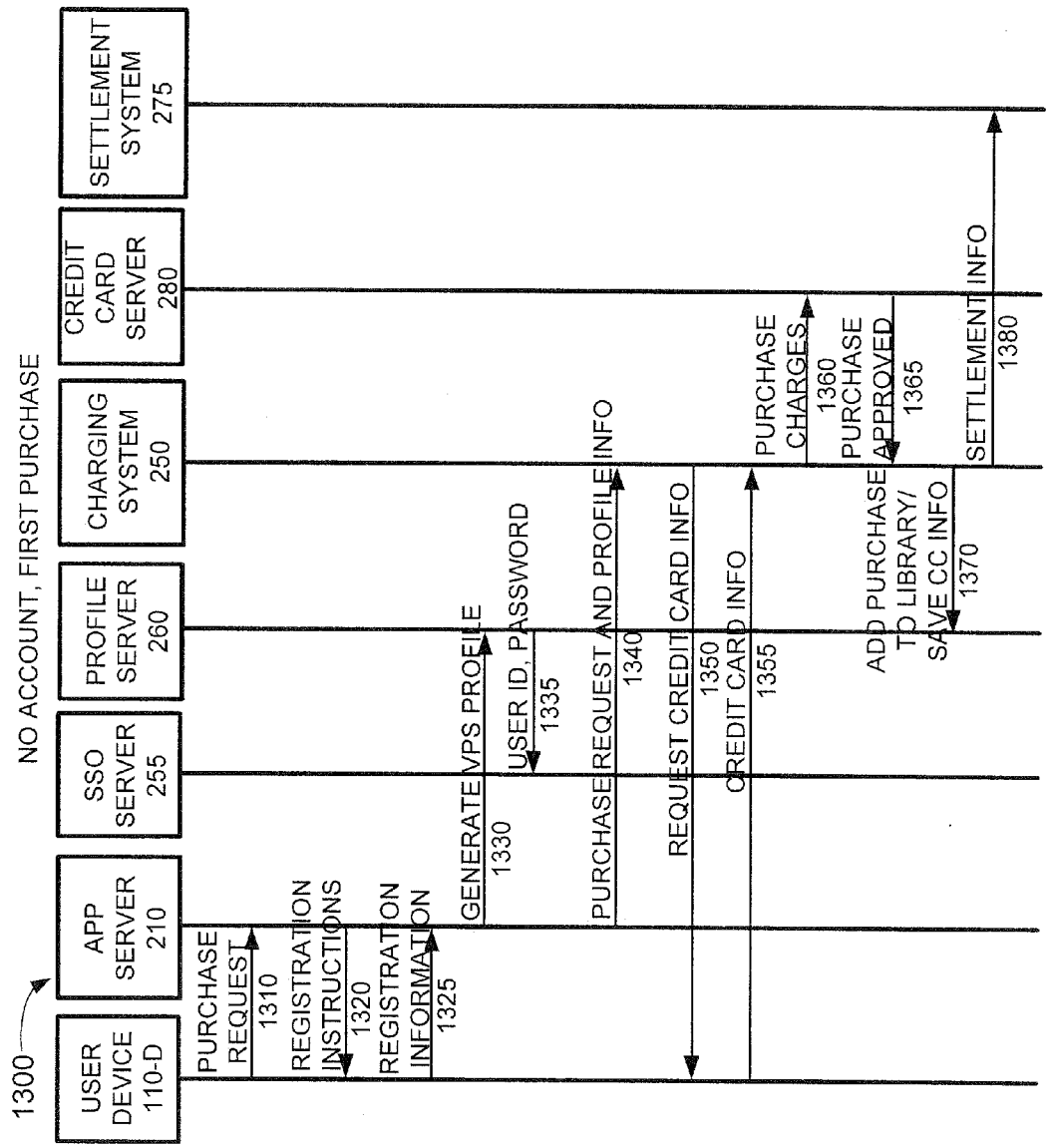
FIG. 13 is a diagram of an example signal flow of a first online purchase of video content for a customer that does not have an existing account according to an implementation described herein.

FIG. 13 is a diagram of an example signal flow 1300 of a first online purchase of video content for a customer that does not have an existing account according to an implementation described herein. As shown in FIG. 13, example signal flow 1300 may include user device 110-D sending a purchase request to application server 210 (signal 1310). User device 110-D may correspond to, for example, a personal computer. The user may have accessed a web page corresponding to a public store front associated with application server 210. The public store front web page may allow the user of user device 110-D to browse a catalog of video assets of VPS 120. The user may select to purchase an episode of a television show available in the catalog.

As the user has not signed in using SSO server 255, application server 210 may, upon receiving the purchase request, present a login page that allows a user to either log in or register. As the user does not have an account of any kind in association with VPS 120, the user may select to register. Application server 210 may provide registration instructions to user device 110-D (signal 1320). The user may enter requested registration information, such as a username and password, which will correspond to the user's SSO credentials (signal 1325).

Application server 210 may instruct profile server 260 to generate a VPS profile for the user (signal 1330). The VPS profile may identify an account type associated with the VPS profile as "online only," indicating that no other account, such as a bundles services account or a voice services account, is associated with the VPS account. Once the VPS profile is created, profile server 260 may provide the SSO credentials to SSO server 255 (1335). Thus, the user may be able to sign in with application server 210 in the future, and application server 210 may be able to authenticate the user via SSO server 255.

Application server 210 may provide information about the purchase request, along with information about the user's VPS profile, to charging system 250 (signal 1340). The VPS profile may Charging system 250 may compute charges for the purchase. Charging system 250 may obtain information from catalog server 235 during computation of the charges (not shown in FIG. 13). Charging system 250 may further determine, based on the account type information, that no other account is associated with the VPS account. Therefore, charging system 250 may not request any account information from ordering system 265. Rather, charging system 250 may request credit card information from user device 110-D (signal 1350). The user may enter the requested credit card information and user device 110-D may send the credit card information to charging system 250 (signal 1355). Charging system 250 may submit the charges and the credit card information to credit card server 280 (signal 1360) and credit card server 280 may respond with an indication that the purchase has been approved (signal 1365).

Charging system 250 may further send information about the purchase to profile server 260 (signal 1370). Profile server 260 may add the video asset to the library associated with the generated VPS account. Charging system 250 may also provide the credit card information to profile server 260 and profile server 260 may save the credit card information in the VPS profile associated with the user. Charging system 250 may further calculate a settlement payment associated with the purchase and may provide settlement payment information to settlement system 275 (signal 1380). Settlement system 275 may settle a payment with content provider 130, associated with the purchased video asset, based on the received settlement information.

Figure 14:
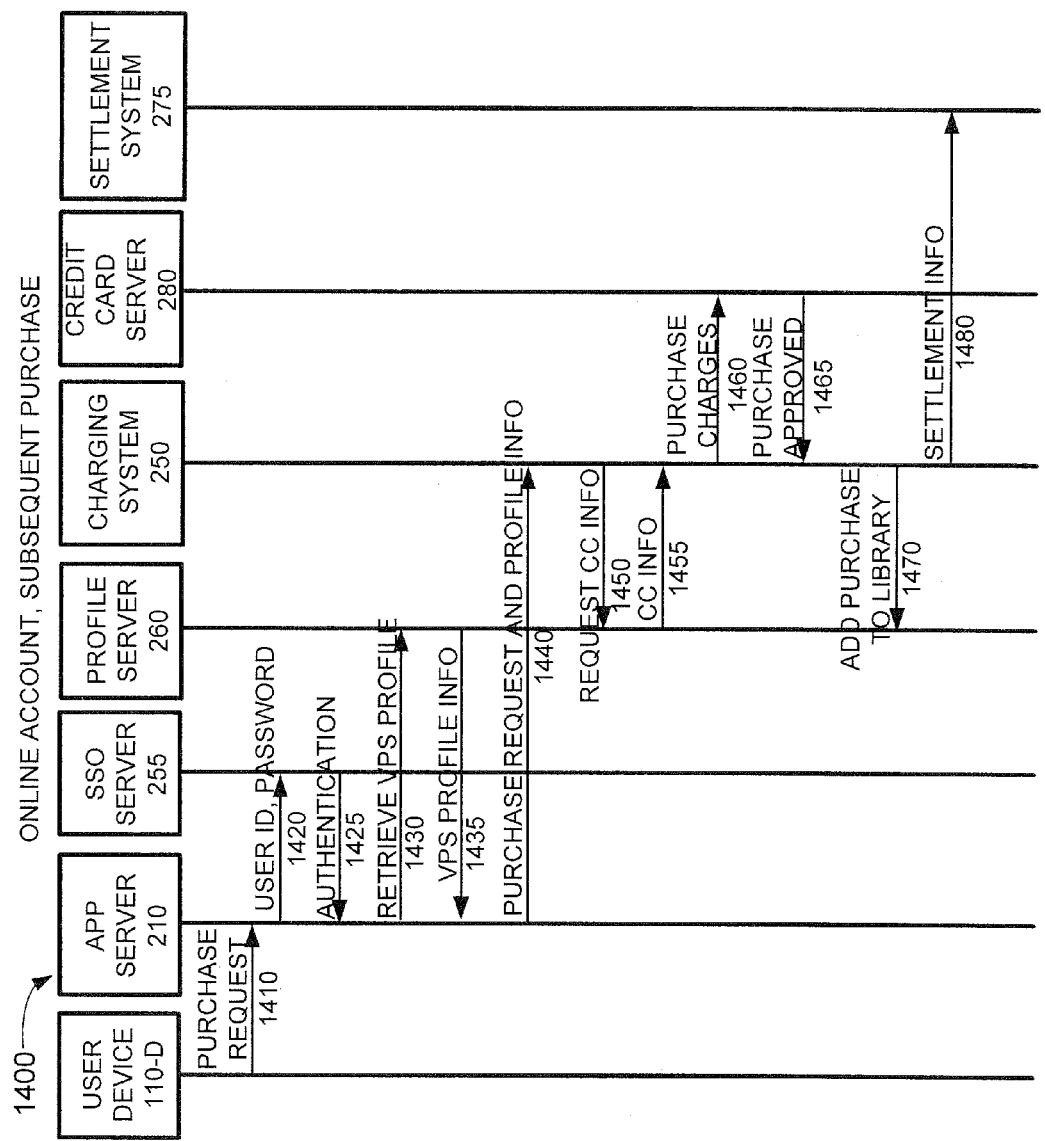
FIG. 14 is a diagram of an example signal flow of a subsequent online purchase of video content according to an implementation described herein.

FIG. 14 is a diagram of an example signal flow 1400 of a subsequent online purchase of a video asset according to an implementation described herein. Furthermore, FIG. 14 may also illustrate the example of a user that used to have another type of account, such as a bundled services account or a voice services account, and that has canceled the other account. When a user with a bundled services account or a voice services account purchases a video asset through VPS 120, the video asset may need to be available to the user even if the user cancels the bundled services account or the voice services account. In such a case, the user's VPS account remains active and the account type in the user's VPS account may be converted to an "online only" account.

As shown in FIG. 14, example signal flow 1400 may include user device 110-D sending a purchase request to application server 210 (signal 1410). For example, the user of user device 110-D may request to purchase another video asset. If the user has not logged in yet, application server 210 may authenticate the user with SSO server 255 (signal 1420) and SSO server 255 may authenticate the user (signal 1425).

Application server 210 may subsequently request a VPS profile from profile server 260 (signal 1430). The request may include the SSO credentials associated with user device 110-D. Since the customer has made a previous purchase of a video asset using VPS system 120, a VPS profile has been previously created for the customer. Thus, profile server 260 may access profile memory 610, may identify a VPS profile associated with user device 110-D based on the SSO credentials, and may provide information from the VPS profile to application server 210 (signal 1440).

In response to receiving information from the VPS profile, application server 210 may send a request to charging system 250 (signal 1440). The request may include information about the purchase, including information identifying the movie and that the type of purchase. Additionally, the request may include information identifying the VPS profile as being an "online only" account.

Charging system 250 may compute charges for the purchase. Charging system 250 may obtain information from catalog server 235 during computation of the charges (not shown in FIG. 14). Charging system 250 may, based on the fact that the VPS profile is an "online only" account, request stored credit card information from profile server 260 (signal 1450). Assuming credit card information has been previously stored in the VPS profile, profile server 260 may provide the credit card information to charging system 250 (signal 1455).

Charging system 250 may submit the charges and the credit card information to credit card server 280 (signal 1460) and credit card server 280 may respond with an indication that the purchase has been approved (signal 1465).

Charging system 250 may further send information about the purchase to profile server 260 (signal 1470). Profile server 260 may add the video asset to the library associated with the generated VPS account. Charging system 250 may further calculate a settlement payment associated with the purchase and may provide settlement payment information to settlement system 275 (signal 1480). Settlement system 275 may settle a payment with content provider 130, associated with the purchased video asset, based on the received settlement information.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 7 and 8A-8E, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
   receiving, by a video provisioning system, a request to purchase a video asset from a user device;
   determining, by the video provisioning system, an account type associated with the user device from a plurality of different account types;
   billing, by the video provisioning system, the purchase to a bundled services account, wherein the bundled services account is associated with one or more of a television service, a data connection service, or a telephone service available over a same connection, when in response to determining that the account type corresponds to the bundled services account;
   billing, by the video provisioning system, the purchase to a voice services account, wherein the voice services account corresponds to a mobile telephone service or a legacy landline telephone service, in response to determining that the account type corresponds to the voice services account; and
   processing, by the video provisioning system, a payment for the purchase via an online payment service, in response to determining that the user device is not associated with a bundled services account or a voice services account;
   where determining the account type associated with the user device includes:
   requesting information about a video provisioning system profile associated with the user device from a profile server that maintains video provisioning system profiles; and
   receiving the account type from the profile server in response to requesting the information.

2. A method comprising:
   receiving, by a video provisioning system, a request to purchase a video asset from a user device;

determining, by the video provisioning system, an account type associated with the user device from a plurality of different account types;

billing, by the video provisioning system, the purchase to a bundled services account, wherein the bundled services account is associated with one or more of a television service, a data connection service, or a telephone service available over a same connection, when in response to determining that the account type corresponds to the bundled services account;

billing, by the video provisioning system, the purchase to a voice services account, wherein the voice services account corresponds to a mobile telephone service or a legacy landline telephone service, in response to determining that the account type corresponds to the voice services account; and processing, by the video provisioning system, a payment for the purchase via an online payment service, in response to determining that the user device is not associated with a bundled services account or a voice services account;

where determining the account type associated with the user device includes:

requesting information about a video provisioning system profile associated with the user device from a profile server that maintains video provisioning system profiles;

and the method further comprising:

receiving an indication from the profile server that the user device is not associated with a video provisioning system profile; and generating a video provisioning system profile for the user device, when the user device is not associated with a video provisioning system profile.

3. The method of claim 2, where generating the video provisioning system profile for the user device includes:

requesting information about an account associated with the user device from an ordering system, where the ordering system maintains information about at least one of bundled services accounts or voice services accounts;

receiving information from the ordering system about an account associated with the user device; and generating the video provisioning system profile for the user device based on the information received from the ordering system about the account associated with the user device.

4. The method of claim 3, where requesting information about the account associated with the user device from the ordering system includes at least one of:

providing a set top box identifier to the ordering system, providing a mobile device identifier to the ordering system, or providing a username to the ordering system.

5. The method of claim 2, where generating the video provisioning system profile for the user device includes:

determining that the user device is not associated with a bundled services account or a voice services account; and sending a request to the user device to register for a video provisioning system profile, in response to determining that the user device is not associated with a bundled services account or a voice services account.

6. A method comprising:

receiving, by a video provisioning system, a request to purchase a video asset from a user device;

determining, by the video provisioning system, an account type associated with the user device from a plurality of different account types;

billing, by the video provisioning system, the purchase to a bundled services account, wherein the bundled services account is associated with one or more of a television service, a data connection service, or a telephone service available over a same connection, when in response to determining that the account type corresponds to the bundled services account;

billing, by the video provisioning system, the purchase to a voice services account, wherein the voice services account corresponds to a mobile telephone service or a legacy landline telephone service, in response to determining that the account type corresponds to the voice services account; and processing, by the video provisioning system, a payment for the purchase via an online payment service, in response to determining that the user device is not associated with a bundled services account or a voice services account;

where billing the purchase to a bundled services account includes:

computing charges for the purchase of the video asset;

performing a credit check with a billing system that handles bills for the bundled services account to determine whether the bundled services account has enough credit for the purchase of the video asset;

receiving a confirmation from the billing system that the bundled services account has enough credit for the purchase of the video asset; and instructing the billing system to add the computed charges to a next bill associated with the bundled services account, when the bundled services account has enough credit for the purchase of the video asset.

7. A method comprising:

receiving, by a video provisioning system, a request to purchase a video asset from a user device;

determining, by the video provisioning system, an account type associated with the user device from a plurality of different account types;

billing, by the video provisioning system, the purchase to a bundled services account, wherein the bundled services account is associated with one or more of a television service, a data connection service, or a telephone service available over a same connection, when in response to determining that the account type corresponds to the bundled services account;

billing, by the video provisioning system, the purchase to a voice services account, wherein the voice services account corresponds to a mobile telephone service or a legacy landline telephone service, in response to determining that the account type corresponds to the voice services account; and processing, by the video provisioning system, a payment for the purchase via an online payment service, in response to determining that the user device is not associated with a bundled services account or a voice services account;

where billing the purchase to a voice services account includes:

computing charges for the purchase of the video asset;

performing a credit check with a billing system that handles bills for the voice services account to determine whether the voice services account has enough credit for the purchase of the video asset;

receiving a confirmation from the billing system that the voice services account has enough credit for the purchase of the video asset; and instructing the billing system to add the computed charges to a next bill associated with the voice services account, when the voice services account has enough credit for the purchase of the video asset.

8. A video provisioning system comprising:

one or more server devices to:

receive a request to purchase a video asset from a user device;

determine an account type associated with the user device from a plurality of different account types;

bill the purchase to a bundled services account, wherein the bundled services account is associated with one or more of a television service, a data connection service, or a telephone service available over a same connection, in response to determining that the account type corresponds to the bundled services account;

bill the purchase to a voice services account, wherein the voice services account corresponds to a mobile telephone service or a legacy landline telephone service, in response to determining that the account type corresponds to the voice services account; and processing a payment for the purchase via an online payment service, in response to determining that the user device is not associated with a bundled services account or a voice services account;

where, when the one or more server devices are to determine the account type associated with the user device, the one or more server devices are further to:

request information about a video provisioning system profile associated with the user device from a profile server that maintains video provisioning system profiles; and receive the account type from the profile server in response to requesting the information.

9. A video provisioning system comprising:

one or more server devices to:

receive a request to purchase a video asset from a user device;

determine an account type associated with the user device from a plurality of different account types;

bill the purchase to a bundled services account, wherein the bundled services account is associated with one or more of a television service, a data connection service, or a telephone service available over a same connection, in response to determining that the account type corresponds to the bundled services account;

bill the purchase to a voice services account, wherein the voice services account corresponds to a mobile telephone service or a legacy landline telephone service, in response to determining that the account type corresponds to the voice services account; and processing a payment for the purchase via an online payment service, in response to determining that the user device is not associated with a bundled services account or a voice services account;

where, when the one or more server devices are to bill the purchase to a bundled services account, the one or more server devices are to:

compute charges for the purchase of the video asset;

perform a credit check with a billing system that handles bills for the bundled services account to determine whether the bundled services account has enough credit for the purchase of the video asset;

receive a confirmation from the billing system that the bundled services account has enough credit for the purchase of the video asset; and instruct the billing system to add the computed charges to a next bill associated with the bundled services account, when the bundled services account has enough credit for the purchase of the video asset.

10. A video provisioning system comprising:

one or more server devices to:

receive a request to purchase a video asset from a user device;

determine an account type associated with the user device from a plurality of different account types;

bill the purchase to a bundled services account, wherein the bundled services account is associated with one or more of a television service, a data connection service, or a telephone service available over a same connection, in response to determining that the account type corresponds to the bundled services account;

bill the purchase to a voice services account, wherein the voice services account corresponds to a mobile telephone service or a legacy landline telephone service, in response to determining that the account type corresponds to the voice services account; and processing a payment for the purchase via an online payment service, in response to determining that the user device is not associated with a bundled services account or a voice services account;

where, when the one or more server devices are to bill the purchase to a voice services account, the one or more server devices are to;

compute charges for the purchase of the video asset;

perform a credit check with a billing system that handles bills for the voice services account to determine whether the voice services account has enough credit for the purchase of the video asset;

receive a confirmation from the billing system that the voice services account has enough credit for the purchase of the video asset; and instruct the billing system to add the computed charges to a next bill associated with the voice services account, when the voice services account has enough credit for the purchase of the video asset.

* * * * *